United States Patent
Li et al.

(10) Patent No.: US 8,962,621 B2
(45) Date of Patent: Feb. 24, 2015

(54) ARALKYL DIAMINE DERIVATIVES AND USES THEREOF AS ANTIDEPRESSANTS

(75) Inventors: Jianqi Li, Shanghai (CN); Yongyong Zheng, Shanghai (CN); Yunfeng Liao, Shanghai (CN); Yali Li, Shanghai (CN)

(73) Assignee: Shanghai Institute of Pharmaceutical Industry, Shanghai (CN)

( * ) Notice: Subject to any disclaimer, the term of this patent is extended or adjusted under 35 U.S.C. 154(b) by 0 days.

(21) Appl. No.: 13/697,389

(22) PCT Filed: May 13, 2011

(86) PCT No.: PCT/CN2011/074029
§ 371 (c)(1),
(2), (4) Date: Dec. 6, 2012

(87) PCT Pub. No.: WO2011/140998
PCT Pub. Date: Nov. 17, 2011

(65) Prior Publication Data
US 2013/0072488 A1 Mar. 21, 2013

(30) Foreign Application Priority Data
May 13, 2010 (CN) .......................... 2010 1 0174743

(51) Int. Cl.
C07D 413/06 (2006.01)
C07D 209/14 (2006.01)
C07D 295/02 (2006.01)
C07D 295/073 (2006.01)
C07D 295/13 (2006.01)
C07D 307/81 (2006.01)
C07D 317/58 (2006.01)
C07D 333/20 (2006.01)
C07D 333/58 (2006.01)
C07D 207/06 (2006.01)
C07D 241/04 (2006.01)
C07D 265/30 (2006.01)

(52) U.S. Cl.
CPC ............ *C07D 413/06* (2013.01); *C07D 209/14* (2013.01); *C07D 295/02* (2013.01); *C07D 295/073* (2013.01); *C07D 295/13* (2013.01); *C07D 307/81* (2013.01); *C07D 317/58* (2013.01); *C07D 333/20* (2013.01); *C07D 333/58* (2013.01); *C07D 207/06* (2013.01); *C07D 241/04* (2013.01); *C07D 265/30* (2013.01)
USPC ........................................ 514/235.5; 544/141

(58) Field of Classification Search
USPC ........................................ 514/235.5; 544/141
See application file for complete search history.

(56) References Cited

U.S. PATENT DOCUMENTS
2005/0267121 A1 12/2005 Li et al.

FOREIGN PATENT DOCUMENTS
CN 1384102 A 12/2002
EP 2305644 A1 4/2011
WO 2009149649 A1 12/2009

OTHER PUBLICATIONS

Land et al., Org. Biomol. Chem., 2003, 3120-3124.*
Kapil et al. Indian J. Chem., vol. 4, Apr. 1966, pp. 177-187.*
Int'l Search Report issued Aug. 18, 2011 in Int'l Application No. PCT/CN2011/074029.

* cited by examiner

*Primary Examiner* — Rebecca Anderson
(74) *Attorney, Agent, or Firm* — Pantich Schwarze Belisario & Nadel LLP

(57) ABSTRACT

Aralkyl diamine derivative of the following formula, pharmaceutically acceptable salts or uses thereof as antidepressants. The derivatives have triplex inhibiting activities of the reuptake of 5-HT, dopamine and noradrenalin, which can be administered to the patients in need of such treatment in the form of compositions orally or injectedly et al.

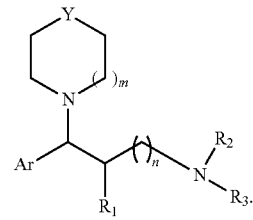

11 Claims, No Drawings

ARALKYL DIAMINE DERIVATIVES AND USES THEREOF AS ANTIDEPRESSANTS

This application is a Section 371 of International Application No. PCT/CN2011/074029, filed May 13, 2011, which was published in the Chinese language on Nov. 17, 2011, under International Publication No. WO 2011/140998 A1, and the disclosure of which is incorporated herein by reference.

TECHNICAL FIELD

The present invention relates to an aralkyl diamine derivative and the use thereof as an antidepressant.

BACKGROUND

Depression is a most common mental disorder with a morbidity of around 5% of the world's population harming the physical and mental health of human beings as well as seriously affecting people's quality of life. It is predicted that by 2020, depression will be the second major disease causing health problems and life span shortening of human beings.

The mechanism about how antidepressants function is not yet well elucidated. Medications with explicit effects on depression are substantially targeting the synapses on the nerve terminals and exert therapeutic roles by regulating the level of synaptic cleft neurotransmitters. Biochemical research on etiology of depression indicates that the depression is mainly related to the following 5 types of neurotransmitters among others: 5-hydroxy tryptamine (5-HT), noradrenaline (NA), dopamine (DA), acetylcholine (Ach) and γ-aminobutyric acid (GABA).

Antidepressants can be categorized into two families: the early non-selective antidepressants and the novel selective reuptake inhibitors. Non-selective antidepressants mainly include the monoamine oxidase inhibitors (MAOIs) and tricyclic antidepressants (TCAs). Selective reuptake inhibitors are comprised of (1) selective serotonin (5-HT) reuptake inhibitors (SSRIs), such as Fluoxetine and Paroxetine; (2) noradrenaline reuptake inhibitors (NRIs) such as Reboxitine; (3) noradrenaline and dopamine reuptake inhibitors (NDRIs) such as Mirtazapine; (4) 5-HT and NA dual reuptake inhibitors (SNRIs) such as Venlafaxine and Duloxetine; (5) 5-HT reuptake enhancers such as Tianeptine et al.

Although a variety of antidepressants are used clinically, the development thereof is still a hotspot in the research on novel drugs due to several factors including that some of the medications have low response rate and potential adverse effect, and that there are still considerable patients who have not been treated effectively with all kinds of medications and some of whom may even require the use of electro-convulsive therapy. Vast amount of fundings from many pharmaceutical companies has been invested into the development of a more promising drug.

The global research trend in antidepressant development mainly lies in two aspects:

One is the secondary development of the existing drugs including 1) further exploiting their new indications and 2) changing the present dosage forms of the existing drugs.

The other is the development of new products. Novel antidepressants with better antidepressive effects, shorter onset time of drug and greater safty than the commercially available drugs can be developed by searching for compounds of new structural type which will act on a new target of multiple targets of this specific disease.

Research on the selective triple reuptake inhibitors, among others coducted on new antidepressants, is now getting more and more attention and is expected to solve the problem about delayed effects that the present antidepressants have, to improve efficacies and to enhance the safty of the drugs. Triple reuptake inhibitors also known as "broad spectrum" antidepressants are referred to a class of compound which simultaneously and selectively inhibit the reuptake of three monoamine neurotransmitters that are closely associated with the depression, namely 5-HT, NA and DA.

Studies on triple reuptake inhibitors are still in the clinical phase. For example, a triple reuptake inhibitor DOV-21947 developed by DOV Pharmaceutical. Inc. is in phase II clinical trial and NS-2359 co-developed by GSK and NeuroSearch is in phase II clinical trial as well. These triple reuptake inhibitors of monoamine neurotransmitter with the advantages of high efficiency, fast onset of action and so on, are becoming the primary focus in the andepressant field. In our country, research and development about novel antidepressive drugs is still in the preliminary stage. Research on novel antidepressants, especially on those targeting the triple pathway of the 5-HT, NA and DA system, becomes an important subject and is currently attracting numerous interests.

THE CONTENT OF THE INVENTION

One purpose of the present invention is to disclose a class of aralkyl diamine derivative designed to overcome defects of antidepressants identified in the prior art such as slow onset of action, low efficacy, great side effect, poor safty, and the like, so as to meet the needs present in the antidepression treatment.

A second purpose of the present invention is to disclose the use of the above-mentioned derivatives as an antidepressant.

The aralkyl diamine derivatives according to the present invention are compounds of the following general formula, and the salts thereof in which 0.5-3 molecules of crystal water are contained.

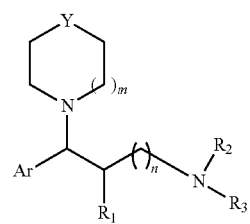

wherein
Ar represents

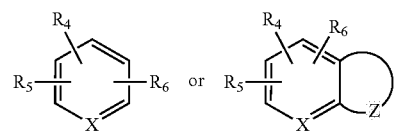

or optionally substituted heteroaryl radicals selected from a group of consisting of thienyl, furyl, pyrimidinyl, pyridazinyl, pyrazinyl, oxazolyl, isoxazolyl, thiazolyl, isothiazolyl, imidazolyl and pyrazolyl, and Ar can not be un-substituted phenyl;

$R_1$ represents H or $C_1$-$C_5$ alkyl;

R₂ and R₃ are each independently one of H, $C_1$-$C_5$ alkyl, $C_1$-$C_5$ haloalkyl, $C_1$-$C_5$ hydroxyalkyl, $C_1$-$C_5$ alkoxy, $C_5$ or $C_6$ alphatic ring, phenyl, substituted phenyl, benzyl or substituted benzyl and the like, with the proviso that R₂ and R₃ are not H at the same time;

or R₂, R₃ and N form together a 5- to 7-membered alphatic ring which may contain one N or O or S and the N may be substituted with R₇;

R₄, R₅ and. R₆ are each independently one of H, $C_1$-$C_3$ alkyl or alkoxy, $C_1$-$C_3$ haloalkyl, $C_1$-$C_3$ haloalkoxy, benzyloxy, $C_5$ or $C_6$ alphatic ring, phenyl, substituted phenyl, hydroxyl, amino, substituted amino, halogen, carboxyl, carboxylic acid ester, nitro or cyano, and the like;

R₇ represents one of $C_1$-$C_5$ alkyl, $C_1$-$C_5$ haloalkyl, $C_1$-$C_5$ hydroxyalkyl, $C_1$-$C_5$ alkoxy, $C_5$ or $C_6$ alphatic ring, phenyl, substituted phenyl, benzyl or substituted benzyl and the like;

Y represents C, N and O; wherein N may be substituted with $C_1$-$C_3$ alkyl, $C_1$-$C_3$ haloalkyl, $C_1$-$C_3$ hydroxyalkyl, phenyl, substituted phenyl, benzyl, substituted benzyl, aromatic heterocyclic or substituted aromatic heterocyclic;

the said substituted phenyl or substituted benzyl has 1-4 substituents on the benzene ring, with R₄, R₅ and R₆ representing the said substituent;

the said substituted amino group is an amino group with $C_1$-$C_3$ alkyl or $C_1$-$C_3$ haloalkyl on the N;

X represents C and N;

Z represents a 5- or 6-membered saturated or unsaturated ring containing C, S, N or O;

m=0, 1, 2; n=1, 2; and the preferred compounds include:

VI-1
N,N-diethyl-3-(3,4-dichlorophenyl)-3-(pyrrolidin-1-yl)-propylamine,

VI-2
N,N-dimethyl-3-(3,4-dichlorophenyl)-3-(pyrrolidin-1-yl)-propylamine,

VI-3
N,N-dimethyl-3-(3,4-dichlorophenyl)-3-(piperazin-1-yl)-propylamine,

VI-4
N,N-dimethyl-3-(3,4-dichlorophenyl)-3-morpholinyl-propylamine,

VI-5
N-methyl-N-benzyl-3-(3,4-dichlorophenyl)-3-morpholinyl-propylamine,

VI-6 4-(3-(3,4-dichlorophenyl)-3-(pyrrolidin-1-yl)propyl morpholine,

VI-7 N,N-dimethyl-3-(3,4-dichlorophenyl)-3-piperidyl-propylamine,

VI-8 N,N-dimethyl-3-(4-chlorophenyl)-3-morpholinyl-propylamine,

VI-9 4-(3-(4-chlorophenyl)-3-(pyrrolidin-1-yl)propyl morpholine,

VI-10 N,N-dimethyl-3-(4-methylphenyl)-3-morpholinyl-propylamine,

VI-11
4-(3-(4-methylpiperazin-1 -yl)-1-(4-methylphenyl)propyl morpholine,

VI 12 4-(3-(4-methylphenyl)-3-(morpholinyl)propylpyrrole,

VI-13
N,N-dimethyl-3-(benzothiophen-3-yl)-3-(pyrrolidin-1-yl)-propylamine,

VI-14
N-methyl-N-benzyl-3-(benzothiophen-3-yl)-3-(pyrrolidin-1-yl)-propylamine,

VI-15
N-methyl-3-(benzothiophen-3-yl)-3-(pyrrolidin-1-yl)-propylamine,

VI-16 N,N-dimethyl-3-(benzothiophen-3-yl)-3-piperidyl-propylamine,

VI-17
N-methyl-N-benzyl-3-(benzothiophen-3-yl)-3-piperidyl-propylamine,

VI-18 N-methyl-3-(benzothiophen-3-yl)-3-piperidyl-propylamine,

VI-19
N,N-dimethyl-3-(benzothiophen-2-yl)-3-(pyrrolidin-1-yl)-propylamine,

VI-20
N-methyl-N-benzyl-3-(benzothiophen-2-yl)-3-(pyrrolidin-1-yl)-propyl amine

VI-21
N-methyl-3-(benzothiophen-2-yl)-3-(pyrrolidin-1-yl)-propylamine,

VI-22
N,N-dimethyl-3-(benzothiophen-2-yl)-3-piperidinyl-propylamine,

VI-23
N-methyl-N-benzyl-3-(benzothiophen-2-yl)-3-piperidyl-propylamine,

VI-24 N-methyl-3-(benzothiophen-2-yl)-3-piperidyl-propylamine,

VI-25
N,N-dimethyl-3-(benzothiophen-2-yl)-3-morpholinyl-propylamine,

VI-26
N-methyl-N-benzyl-3-(benzothiophen-2-yl)-3-morpholinyl-propylamine,

VI-27 N-methyl-3-(benzothiophen-2-yl)-3-morpholinyl-propylamine,

VI-28
N,N-dimethyl-3-(benzothiophen-3-yl)-3-morpholinyl-propylamine,

VI-29
N-methyl-N-benzyl-3-(benzothiophen-3-yl)-3-morpholinyl-propylamine,

VI-30 N-methyl-3-(benzothiophen-3-yl)-3-morpholinyl-propylamine,

VI-31 N,N-dimethyl-3-(indol-3-yl)-3-morpholinyl-propylamine,

VI-32 N-methyl-N-benzyl-3-(indol-3-yl)-3-morpholinyl-propylamine,

VI-33 N-methyl-3-(indol-3-yl)-3-morpholinyl-propylamine,

VI-34
N,N-dimethyl-3-(5-chloro-6-methoxynaphthalen-2-yl)-3-morpholinyl-propylamine, VI-35 N-methyl-N-benzyl-3-(5-chloro-6-methoxynaphthalen-2-yl)-3-morpholinyl-propylamine, VI-36
N,N-dimethyl-3-(5-chloro-6-methoxynaphthalen-2-yl)-3-(pyrrolidin-1-yl)-propylamine, VI-37
N,N-dimethyl-3-(4-methoxyphenyl)-3-(pyrrolidin-1-yl)-propylamine, VI-38 N,N-dimethyl-3-(4-methoxyphenyl)-3-morpholinyl-propylamine, VI-39
N,N,2-trimethyl-3-(4-methoxyphenyl)-3-morpholinyl-propylamine, VI-40 N,N-dimethyl-24(3,4-dichlorophenyl)(morpholine)methyl)-1-heptylamine,
VI-41 N,N-dimethyl-3-(2,3-dihydrobenzofuran-5-yl)-3-morpholinyl-propylamine,
VI-42 N-methyl-N-benzyl-3-(2,3-dihydrobenzofuran-5-yl)-3-morpholinyl-propylamine,
VI-43 N-methyl-3-(2,3-dihydrobenzofuran-5-yl)-3-morpholinyl-propylamine,
VI-44 N,N-dimethyl-4-(3,4-dichlorophenyl)-4-morpholinyl-butylamine,
VI-45 N,N-dimethyl-4-(3,4-dichlorophenyl)-4-(piperazin-1-yl)-butylamine,
VI-46 N,N-dimethyl-4-(benzothiophen-3-yl)-4-morpholinyl-butylamine,
VI-47 N,N-dimethyl-4-(benzothiophen-3-yl)-4-(piperazin-1-yl)-butylamine,
VI-48 N,N-dimethyl-3-(2,4-difluorophenyl)-3-morpholinyl-propylamine,
VI-49 N-methyl-N-benzyl-3-(2,4-difluorophenyl)-3-morpholinyl-propylamine,
VI-50 N-methyl-3-(2,4-difluorophenyl)-3-morpholinyl-propylamine,
VI-51 N,N-dimethyl-3-(3,4-dichlorophenyl)-3-(4-benzylpiperazinyl)-propylamine,
VI-52 N,N-dimethyl-3-(3,4-dichlorophenyl)-3-(4-(3-(trifluoromethyl)phenyl)piperazinyl)-propylamine,
VI-53 N-methyl-N-benzyl-3-(1,2-methylenedioxybenzen-4-yl)-3-piperidyl-propylamine,
VI-54 N-methyl-3-(1,2-methylenedioxybenzen-4-yl)-3-piperidyl-propylamine,
VI-55 N,N-dimethyl-3-(3,4-dimethoxyphenyl)-3-morpholinyl-propylamine,
VI-56 N-methyl-N-benzyl-3-(3,4-dimethoxyphenyl)-3-morpholinyl-propylamine,
VI-57 N-methyl-3-(3,4-dimethoxyphenyl)-3-morpholinyl-propylamine,
VI-58 N,N-dimethyl-3-(3,4-dimethoxyphenyl)-3-piperidyl-propylamine,
VI-59 N-methyl-N-benzyl-3-(3,4-dimethoxyphenyl)-3-piperidyl-propylamine,
VI-60 N-methyl-3-(3,4-dimethoxyphenyl)-3-piperidyl-propylamine,
VI-61 N,N-dimethyl-3-(thien-2-yl)-3-morpholinyl-propylamine,
VI-62 N-methyl-N-benzyl-3-(thien-2-yl)-3-morpholinyl-propylamine,
VI-63 N-methyl-3-(thien-2-yl)-3-morpholinyl-propylamine, or pharmaceutically acceptable salts thereof.

The chemical structures of the above-mentioned compounds are listed in Table 1.

TABLE 1

| No. | Ar | $R_1$ | $R_2$ | $R_3$ | Y | m | n |
|---|---|---|---|---|---|---|---|
| VI-1 | 3,4-dichlorophenyl | H | Et | Et | $CH_2$ | 0 | 1 |
| VI-2 | 3,4-dichlorophenyl | H | Me | Me | $CH_2$ | 0 | 1 |
| VI-3 | 3,4-dichlorophenyl | H | Me | Me | NH | 1 | 1 |
| VI-4 | 3,4-dichlorophenyl | H | Me | Me | O | 1 | 1 |
| VI-5 | 3,4-dichlorophenyl | H | Me | CH$_2$Ph | O | 1 | 1 |
| VI-6 | 3,4-dichlorophenyl | H | \[tetrahydropyran\] | | $CH_2$ | 0 | 1 |

TABLE 1-continued

| No. | Ar | R₁ | R₂ | R₃ | Y | m | n |
|---|---|---|---|---|---|---|---|
| VI-7 | 3,4-dichlorophenyl | H | Me | Me | CH₂ | 0 | 1 |
| VI-8 | 4-chlorophenyl | H | Me | Me | O | 1 | 1 |
| VI-9 | 4-chlorophenyl | H | Me | tetrahydropyran-yl | CH₂ | 0 | 1 |
| VI-10 | 4-methylphenyl | H | Me | Me | O | 1 | 1 |
| VI-11 | 4-methylphenyl | H | Me | N(propyl)₂ | O | 1 | 1 |
| VI-12 | 4-methylphenyl | H | Me | cyclopentyl | O | 1 | 1 |
| VI-13 | benzothiophen-3-yl | H | Me | Me | CH₂ | 0 | 1 |
| VI-14 | benzothiophen-3-yl | H | Me | CH₂Ph | CH₂ | 0 | 1 |
| VI-15 | benzothiophen-3-yl | H | Me | H | CH₂ | 0 | 1 |
| VI-16 | benzothiophen-3-yl | H | Me | Me | CH₂ | 1 | 1 |
| VI-17 | benzothiophen-3-yl | H | Me | CH₂Ph | CH₂ | 1 | 1 |
| VI-18 | benzothiophen-3-yl | H | Me | H | CH₂ | 1 | 1 |
| VI-19 | benzothiophen-2-yl | H | Me | Me | CH₂ | 0 | 1 |

TABLE 1-continued
| No. | Ar | R₁ | R₂ | R₃ | Y | m | n |
|---|---|---|---|---|---|---|---|
| VI-20 | 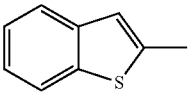 | H | Me |  | CH₂ | 0 | 1 |
| VI-21 | 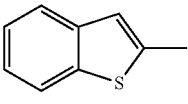 | H | Me | H | CH₂ | 0 | 1 |
| VI-22 | 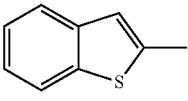 | H | Me | Me | CH₂ | 1 | 1 |
| VI-23 | 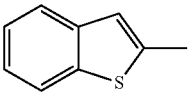 | H | Me |  | CH₂ | 1 | 1 |
| VI-24 | 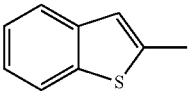 | H | Me | H | CH₂ | 1 | 1 |
| VI-25 | 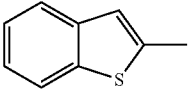 | H | Me | Me | O | 1 | 1 |
| VI-26 | 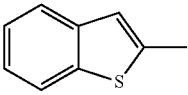 | H | Me |  | O | 1 | 1 |
| VI-27 | 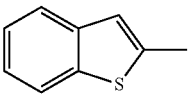 | H | Me | H | O | 1 | 1 |
| VI-28 | 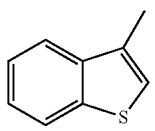 | H | Me | Me | O | 1 | 1 |
| VI-29 | 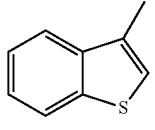 | H | Me |  | O | 1 | 1 |
| VI-30 | 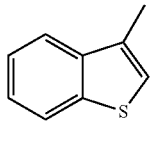 | H | Me | H | O | 1 | 1 |
| VI-31 | 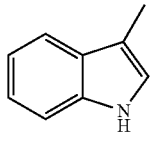 | H | Me | Me | O | 1 | 1 |
| VI-32 | 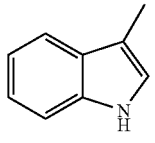 | H | Me |  | O | 1 | 1 |

TABLE 1-continued
| No. | Ar | $R_1$ | $R_2$ | $R_3$ | Y | m | n |
|---|---|---|---|---|---|---|---|
| VI-33 | 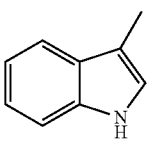 | H | Me | H | O | 1 | 1 |
| VI-34 | 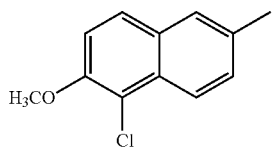 | H | Me | Me | O | 1 | 1 |
| VI-35 | 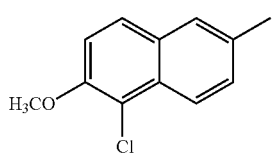 | H | Me |  | O | 1 | 1 |
| VI-36 | 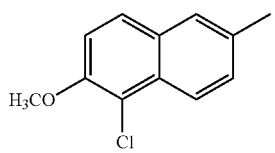 | H | Me | Me | $CH_2$ | 0 | 1 |
| VI-37 | 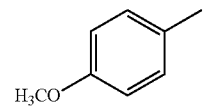 | H | Me | Me | $CH_2$ | 0 | 1 |
| VI-38 | 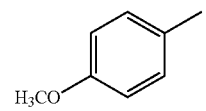 | H | Me | Me | O | 1 | 1 |
| VI-39 | 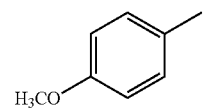 | Me | Me | Me | O | 1 | 1 |
| VI-40 | 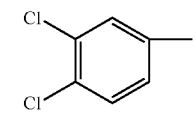 | n-$C_5H_{11}$ | Me | Me | O | 1 | 1 |
| VI-41 | 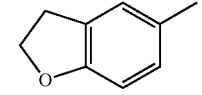 | H | Me | Me | O | 1 | 1 |
| VI-42 | 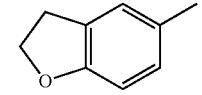 | H | Me |  | O | 1 | 1 |
| VI-43 | 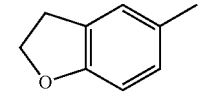 | H | Me | H | O | 1 | 1 |
| VI-44 | 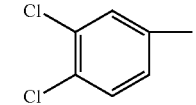 | H | Me | Me | O | 1 | 2 |

TABLE 1-continued
| No. | Ar | R₁ | R₂ | R₃ | Y | m | n |
|---|---|---|---|---|---|---|---|
| VI-45 | 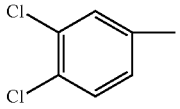 | H | Me | Me | NH | 1 | 2 |
| VI-46 | 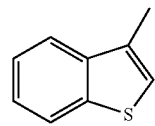 | H | Me | Me | O | 1 | 2 |
| VI-47 | 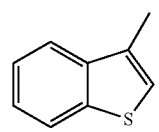 | H | Me | Me | NH | 1 | 2 |
| VI-48 |  | H | Me | Me | O | 1 | 1 |
| VI-49 | 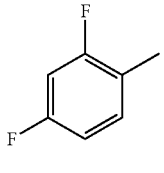 | H | Me |  | O | 1 | 1 |
| VI-50 |  | H | Me | H | O | 1 | 1 |
| VI-51 | 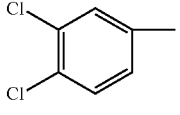 | H | Me | Me |  | 1 | 1 |
| VI-52 | 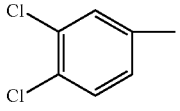 | H | Me | Me | 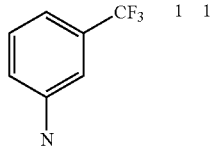 | 1 | 1 |
| VI-53 | 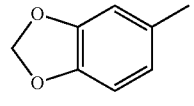 | H | Me |  | CH₂ | 1 | 1 |
| VI-54 | 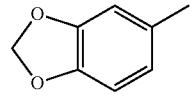 | H | Me | H | CH₂ | 1 | 1 |
| VI-55 | 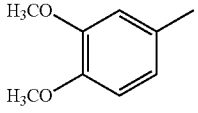 | H | Me | Me | O | 1 | 1 |

TABLE 1-continued

| No. | Ar | R₁ | R₂ | R₃ | Y | m | n |
|---|---|---|---|---|---|---|---|
| VI-56 | 3,4-dimethoxyphenyl | H | Me | CH₂Ph | O | 1 | 1 |
| VI-57 | 3,4-dimethoxyphenyl | H | Me | H | O | 1 | 1 |
| VI-58 | 3,4-dimethoxyphenyl | H | Me | Me | CH₂ | 1 | 1 |
| VI-59 | 3,4-dimethoxyphenyl | H | Me | CH₂Ph | CH₂ | 1 | 1 |
| VI-60 | 3,4-dimethoxyphenyl | H | Me | H | CH₂ | 1 | 1 |
| VI-61 | 2-thienyl | H | Me | Me | O | 1 | 1 |
| VI-62 | 2-thienyl | H | Me | CH₂Ph | O | 1 | 1 |
| VI-63 | 2-thienyl | H | Me | H | O | 1 | 1 |

Compounds of the present invention can be prepared according to a general synthetic method described as follows:

The aromatic ring compound (I) is reacted with a proper acyl chloride compound (VII) under the catalysis of AlCl₃ to give the corresponding halogenated aralkyl-ketone (II) through the F—C reaction. The intermediate (II) is then reacted with a proper amine (VIII) through a substitution reaction to give the intermediate (III), which could also be prepared by Munich reaction with corresponding arone (IV), amine (VIII) and polyformaldehyde. The intermediate (V) prepared by reducing intermediate (III) with NaBH₄ is added with compound (IX) after its reaction with p-toluenesulfonyl chloride to give the final product (VI).

The process is shown in the scheme:

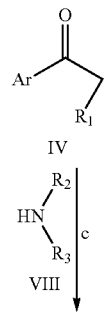

-continued

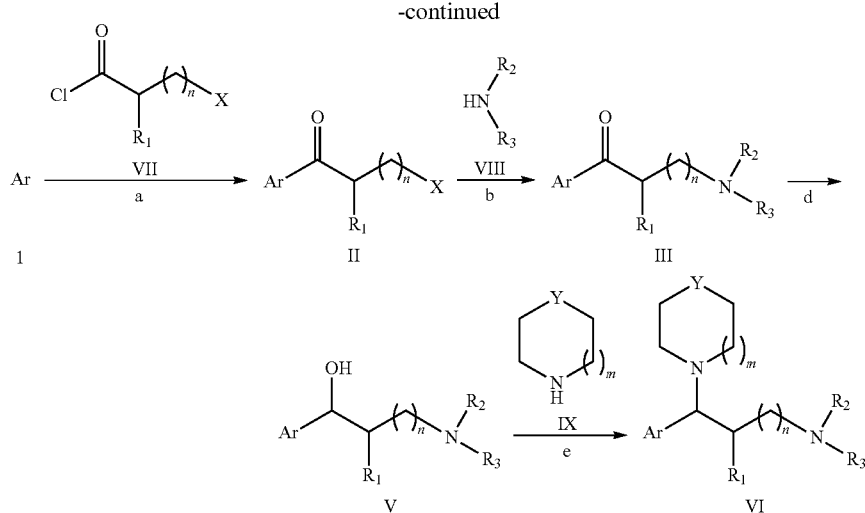

wherein

X=Cl, Br;

Ar, $R_1$, $R_2$, $R_3$, Y, m and n have the same definition as described above; and a: $AlCl_3$, $CH_2Cl_2$; or $AlCl_3$, 70° C.;
b: EtOH, reflux; or $EtN(i-Pr)_2$, $CH_3CN$;
c: polyformaldehyde, concentrated HCl, 95% EtOH;
d: $NaBH_4$, $CH_3OH$;
e: (1)TsCl, $N(Et)_3$; (2) IX, $K_2CO_3$.

The above-mentioned aromatic compound (I), acyl chloride (VII), amine (VIII), arone (IV) and cycloalkanamine (IX) are commercially available or can be prepared from methods in the Examples.

The present invention is related to the said aryl alkanol piperidine derivatives which act as triple reuptake inhibitors for 5-HT, NA and DA and are useful as an antidepressant.

The derivatives of the present invention can be administrated in the form of a composition to a patient in need thereof through oral or injection routes, etc.

The composition comprises a therapeutically effective amount of the above-mentioned compounds or pharmaceutically acceptable salts thereof, and one or more medically acceptable carriers.

The said carriers are referred to carriers conventionally used in the medical field, for example, diluents; excipients, such as water; binders, such as cellulose derivatives, gelatin, polyvinyl pyrrolidone, etc.; fillers, such as starch etc.; disintegrant such as calcium carbonate and sodium bicarbonate. In addition, other adjuvants such as flavors and sweeteners may be added into the composition.

The composition can be formed into conventional solid formulations such as tablets, powder, or capsules for oral administration and into injection forms for injection.

Various dosage forms of the composition of the present invention can be prepared utilizing conventional methods in the medical field, wherein the content of the active ingredient is between 0.1%~99.5% by weight.

The application dose of the present invention varies depending on the administration means, ages and body weights of the patients, the type and the severity of the disease to be treated, etc. The daily dose is 5-30 mg/kg body weight for oral administration or 1-10mg/kg body weight for injection.

It is shown in the animal tests that compounds of the present invention and the salts thereof have antagonist effect on depression.

The derivatives of the present invention by way of antidepressant effect may have better efficacy, broader indication, less toxicity and fewer side effects when compared to the traditional antidepressants or antidepressants with a single-action mechanism.

DETAILED DESCRIPTION OF THE INVENTION

General Method One:
Preparation of the halogenated aralkyl-ketone (II)
Method A:

The aromatic compound (I) (0.2 mol) is dissolved in $CH_2Cl_2$ (200 mL) and added with $AlCl_3$ (0.24 mol) batch by batch in an ice bath while the internal temperature is maintained between 0-5° C. The mixture is stirred for 30 min. Keep the internal temperature below 5° C. and add dropwise a solution of corresponding acyl chloride (VII) (0.22 mol) in $CH_2Cl_2$ (100 mL). After the addition, raise the temperature to the room temperature and let react for 3 h. TLC with ethyl acetate: petroleum ether (1:15) indicates a completion of the reaction. The reaction mixture is then poured into 60 mL ice water under stirring. The organic phase is separated and washed with saturated NaCl solution (50 mL). After dried over anhydrous $MgSO_4$, the organic phase is filtered and then concentrated. A pure product of the halogenated aralkyl-ketone (II) is obtained with a yield of 70-90% by slurrying the concentrate in anhydrous ethanol (50 mL).

Method B:

The aromatic compound (I) (0.2 mol) added with $AlCl_3$ (0.24 mol) is heated to 70° C. and added dropwise the corresponding acyl chloride (VII) (0.2 mol) under stirring. After the addition, a reaction is maintained at 70° C. for 8 h. TLC with ethyl acetate: petroleum ether (1:15) indicates a completion of the reaction. The reaction mixture is cooled to room temperature and added with $CH_2Cl_2$ (100 mL) before it is poured into 50 mL ice water under stirring. The organic phase is separated and washed with saturated NaCl solution (50 mL×1). After dried over anhydrous $MgSO_4$, the organic phase is filtered and then concentrated. A pure product of the halogenated aralkyl-ketone (II) is obtained with a yield of 80-90% by slurrying the concentrate in anhydrous ethanol (50 mL).

General Method Two:

Preparation of Aralkyl-Ketone Amine, the Intermediate (III)

Method A:

A reaction mixture of the halogenated aralkyl-ketone (II) (0.1 mol) and the amine (VIII) (0.5 mol) as a starting material dissolved in anhydrous ethanol (100 mL) is reacted under reflux for 3 h. TLC (dichloromethane: methanol=20:1) indicates a complete consumption of the starting material (II). The solvent is concentrated down till dry. To the residue, dichloromethane (100 mL) and saturated NaCl solution (40 mL) are added, followed by a 20-min stirring. The organic phase is separated and washed with 5 wt % dilute HCl solution (30 mL). After dried over anhydrous $MgSO_4$, the organic phase is filtered and then concentrated to give the crude product which is then dissolved in ethyl acetate (30 mL) and formed a hydrochloride by adding hydrochloric acid alcohol to the mixture. The intermediate (III) is thus obtained with a yield of 70-95% based on the intermediate (II).

Method B:

A reaction mixture of the halogenated aralkyl-ketone (II) (0.1 mol) and the hydrochloride of the amine (VIII) (0.1 mol) as a starting material dissolved in acetonitrile (100 mL) is added with diisopropylethylamine (0.2 mol) and reacted at room temperature for 12 h. TLC (dichloromethane: methanol=20:1) indicates a complete consumption of the starting material (II). The solvent is concentrated down till dry. To the residue, dichloromethane (100 mL) and saturated NaCl solution (40 mL) are added, followed by a 20-min stirring. The organic phase is separated and washed with 5 wt % dilute HCl solution (30 mL). After dried over anhydrous $MgSO_4$, the organic phase is filtered and then concentrated to give the crude product which is then dissolved in ethyl acetate (30 mL) and formed a hydrochloride by adding hydrochloric acid alcohol to the mixture. The intermediate (III) is thus obtained with a yield of 60-85% based on the intermediate (II).

Method C:

A reaction mixture of the aralkyl-ketone (IV) (0.1 mol), the hydrochloride of the corresponding amine (VIII) (0.11 mol) and the polyformaldehyde (0.13 mol) dissolved in 95% ethanol (20 mL) is added with wt % concentrated HCl (0.2 mL) and refluxed for 5 h. TLC (dichloromethane: methanol=20:1) indicates a complete consumption of the starting material (IV). The solvent is concentrated down till dry. To the residue, dichloromethane (100 mL) and saturated $NaHCO_3$ solution (40 mL) are added, followed by a 20-min stirring. The organic phase is separated and washed with 5 wt % dilute HCl solution (30 mL). After dried over anhydrous $MgSO_4$, the organic phase is filtered and then concentrated to give the crude product which is then dissolved in ethyl acetate (30 mL) and formed a hydrochloride by adding hydrochloric acid alcohol to the mixture. The intermediate (III) is thus obtained with a yield of 70-90% based on the intermediate (IV).

General Method Three:

Preparation of aromatic alkanolamine, the intermediate (V)

The intermediate (III) (0.05 mol) is dissolved in methanol (50 mL) and added with $NaBH_4$ (0.05 mol) batch by batch at room temperature. The mixture is stirred for 3 h under the same temperature. TLC (dichloromethane: methanol=15:1) indicates a complete consumption of the starting material (III). The solvent is concentrated down till dry. To the residue, dichloromethane (60 mL) and saturated NaCl solution (30 mL) are added, followed by a 20-min stirring. After separated and dried over anhydrous $MgSO_4$, the organic phase is filtered then concentrated to give the crude product which is then dissolved in ethyl acetate (20 mL) and formed a hydrochloride by adding hydrochloric acid alcohol to the mixture. The intermediate (V) is thus obtained with a yield of 80-95%.

General Method Four:

Preparation of the Aralkyl Diamine Compound (VI)

To the solution of the intermediate (V) (0.03 mol) dissolved in acetonitrile (50 mL), triethylamine (0.036 mol) is first added at room temperature and then is p-methyl benzenesulfonyl chloride (0.033 mol) with stirring. The mixture is reacted at room temperature for 12 h. TLC (dichloromethane: methanol=15:1) indicates a complete consumption of the starting material (V). Then, cycloalkanamine (IX) (0.09 mol) and $K_2CO_3$ (0.03 mol) are added and the reaction is allowed to proceed at room temperature for 8 h. TLC (dichloromethane: methanol=15:1) indicates a completion of the reaction. The solvent is concentrated down till dry. To the residue, dichloromethane (60 mL) and saturated NaCl solution (20 mL) are added, followed by a 20-min stirring. The organic phase is separated and washed with 5 wt % dilute HCl solution (30 mL). After dried over anhydrous $MgSO_4$, the organic phase is filtered and then concentrated to give the crude product which is then dissolved in ethyl acetate (10 mL) and formed a hydrochloride by adding hydrochloric acid alcohol to the mixture. The hydrochloride of the target product (VI) is thus obtained with a yield of 40-60%.

EXAMPLES

Example 1

Preparation of the hydrochloride of N,N-diethyl-3-(3,4-dichlorophenyl)-3-(pyrrolidin-1-yl)-propylamine (VI-1)

$AlCl_3$ (0.1 mol) is added to 1,2-dichlorobenzene (0.1 mol). The mixture is heated to 70° C. and added with 3-chloropropionyl chloride (0.11 mol) dropwise while stirring. Following procedures described in General Method One-Method B, 3-chloro-1-(3,4-dichlorophenyl)-acetone which is a white solid, is obtained (20.5 g). The yield based on 1,2-dichlorobenzene is 86.9%. MS(m/z): 236.1 $[M+1]^+$.

3-chloro-1-(3,4-dichlorophenyl)-acetone (0.05 mol), diethyamine (0.05 mol) and diisopropyl ethylamine (0.1 mol) are dissolved in acetonitrile (100 mL). Following procedures described in General Method Two-Method B, a white solid product is obtained (12.0 g). The yield is 77.7%. MS(m/z): 274.2 $[M+1]^+$.

The product obtained above (10 mmol) and $NaBH_4$ (10 mmol) are dissolved in methanol (50 mL). Following procedures described in General Method Three, a white solid is obtained (2.9 g). The yield is 93.2%. MS(m/z): 276.1 $[M+1]^+$.

The product obtained above (8 mmol), triethylamine (9.6 mmol) and p-methyl benzenesulfonyl chloride (8.8 mmol) are dissolved in acetonitrile (30 mL). Following procedures described in General Method Four, tetrahydropyrrole (24 mmol) and $K_2CO_3$ (8 mmol) are added. The hydrochloride of N,N-diethyl-3-(3,4-dichlorophenyl)-3-(pyrrolidin-1-yl)-propylamine (VI-1) is obtained as a white solid (1.7 g). The yield is 53.1%. Mp=249.3-252.7° C., MS(m/z): 329.2 $[M+1]^+$.

$^1$H NMR (DMSO-$d_6$): δ: 1.13-1.16 (t, J=7.2 Hz, 6H, —NCH$_2$CH$_3$), 1.85-1.98 (m, 4H, —NCH$_2$CH$_2$CH$_2$CH$_2$N—), 2.58-2.61 (m, 2H, —CH$_2$CH$_2$N—), 2.61-2.83 (m, 2H, —NCH$_2$CH$_2$CH$_2$CH$_2$N—), 2.91-2.96 (m, 2H, —CH$_2$CH$_2$N—), 3.06 (m, 4H, —NCH$_2$CH$_3$), 3.19 (m, 1H, —NCH$_2$CH$_2$CH$_2$CH,N—), 3.74 (m, 1H, —NCH$_2$CH$_2$CH$_2$CH$_2$N—), 4.63 (s, 1H, Ar—CH—), 7.75-

7.77 (dd, $J_1$=8.4 Hz, $J_2$=3.2 Hz, 2H, Ar—H), 8.10 (s, 1H, Ar—H), 10.76 (br, 1H, HCl, +$D_2O$ vanished), 12.14 (br, 1H, HCl, +$D_2O$ vanished).

Example 2

Preparation of the hydrochloride of N,N-dimethyl-3-(3,4-dichlorophenyl)-3-(pyrrolidin-1-yl)-propylamine (VI-2)

3-chloro-1-(3,4-dichlorophenyl)-acetone (0.05 mol) and dimethyamine aqueous solution (0.25 mol) are dissolved in anhydrous ethanol (100 mL). Following procedures described in General Method Two-Method A, a white solid product is obtained (11.5 g). The yield is 81.9%. MS(m/z): 246.1 [M+1]$^+$.

The product obtained above (10 mmol) and $NaBH_4$ (10 mmol) are dissolved in methanol (50 mL). Following procedures described in General Method Three, a white solid is obtained (2.65 g). The yield is 93.6%. MS(m/z): 248.1 [M+1]$^+$.

The product obtained from the previous step (8 mmol), triethylamine (9.6 mmol) and p-methyl benzenesulfonyl chloride (8.8 mmol) are dissolved in acetonitrile (30 mL). Following procedures described in General Method Four, tetrahydropyrrole (24 mmol) and $K_2CO_3$ (8 mmol) are added. The hydrochloride of N,N-dimethyl-3-(3,4-dichlorophenyl)-3-(pyrrolidin-1-yl)-propylamine (VI-2) is obtained as a white solid (1.4 g). The yield is 47.0%. Mp=266.5-268.6° C., MS(m/z): 301.2 [M+1]$^+$.

$^1$H NMR ($CDCl_3$-d): δ: 1.80-1.99 (m, 4H, —$NCH_2CH_2CH_2CH_2N$—), 2.54-2.55 (d, J=4.8 Hz, 2H, —$CH_2CH_2N$—), 2.60-2.61 (d, J=4.8 Hz, 2H, —$CH_2CH_2N$—), 2.61 (s, 6H, $N(CH_3)_2$), 2.57-2.70 (m, 1H, —$NCH_2CH_2CH_2CH_2N$—), 2.91-2.92 (m, 1H, —$NCH_2CH_2CH_2CH_2N$—), 3.15-3.17 (m, 1H, —$NCH_2CH_2CH_2CH_2N$—), 3.73-3.74 (m, 1H, —$NCH_2CH_2CH_2CH_2N$—), 4.72 (s, 1H, Ar—CH—), 7.33-7.35 (d, J=8.4 Hz, 1H, Ar—H), 7.68-7.70 (dd, $J_1$=2.0 Hz, $J_2$=8.0 Hz, 1H, Ar—H), 7.82 (d, J=2.0 Hz, 1H, Ar—H), 11.70 (br, 1H, HCl, +$D_2O$ vanished), 12.39 (br, 1H, HCl, +$D_2O$ vanished).

Example 3

Preparation of the hydrochloride of N,N-dimethyl-3-(3,4-dichlorophenyl)-3-(piperazin-1-yl)-propylamine (VI-3)

The hydrochloride of N,N-dimethyl-3-(3,4-dichlorophenyl)-3-hydroxy-propylamine (8 mmol), triethylamine (9.6 mmol) and p-methyl benzenesulfonyl chloride (8.8 mmol) are dissolved in acetonitrile (30 mL). Following procedures described in General Method Four, piperazine (24 mmol) and $K_2CO_3$ (8 mmol) are added. The hydrochloride of N,N-dimethyl-3-(3,4-dichlorophenyl)-3-(piperazin-1-yl)-propylamine (VI-3) is obtained as a white solid (1.7 g). The yield is 50.2%. Mp=257.3-258.9° C., MS(m/z): 316.2 [M+1]$^+$.

$^1$H NMR (DMSO-$d_6$)+$D_2O$: δ: 1.98-2.03 (m, 2H, —$CH_2CH_2N$—), 2.65 (s, 6H, $N(CH_3)_2$), 3.00-3.04 (m, 2H, —$CH_2CH_2N$—), 3.09-3.15 (m, 4H, —$NCH_2CH_2N$—), 3.29-3.35 (m, 4H, —$NCH_2CH_2N$—), 3.78-3.80 (t, J=7.2 Hz, 1H, Ar—CH—), 7.27-7.29 (dd, $J_1$=2.0 Hz, $J_2$=6.8 Hz, 1H, Ar—H), 7.54 (d, J=1.2 Hz, 1H, Ar—H), 7.62-7.65 (d, J=8.4 Hz, 1H, Ar—H).

Example 4

Preparation of the hydrochloride of N,N-dimethyl-3-(3,4-dichlorophenyl)-3-morpholinyl-propylamine (VI4)

The hydrochloride of N,N-dimethyl-3-(3,4-dichlorophenyl)-3-hydroxy-propylamine (8 mmol), triethylamine (9.6 mmol) and p-methyl benzenesulfonyl chloride (8.8 mmol) are dissolved in acetonitrile (30 mL). Following procedures described in General Method Four, morpholine (24 mmol) and $K_2CO_3$ (8 mmol) are added. The hydrochloride of N,N-dimethyl-3-(3,4-dichlorophenyl)-3-morpholinyl-propylamine (VI-4) is obtained according to General Method Four as a white solid (1.62 g). The yield is 52.2%. Mp=172.1-174.8° C., MS(m/z): 317.3 [M+1]$^+$.

$^1$H NMR (DMSO-$d_6$): δ: 1.98-2.42 (m, 2H, —$CH_2CH_2N$—), 2.30-2.40 (m, 4H, —$NCH_2CH_2O$), 2.70 (s, 6H, $N(CH_3)_2$), 3.01-3.08 (m, 2H, —$CH_2CH_2N$—), 3.61-3.65 (m, 4H, —$NCH_2CH_2O$), 3.78-3.81 (t, J=7.2 Hz, 1H, Ar—CH—), 7.26-7.28 (dd, $J_1$=2.0 Hz, $J_2$=6.8 Hz, 1H, Ar—H), 7.53-7.54 (d, J=1.2 Hz, 1H, Ar—H), 7.62-7.64 (d, J=8.4 Hz, 1H, Ar—H), 10.49 (br, 1H, HCl, +$D_2O$ vanished).

Example 5

Preparation of the hydrochloride of N-methyl-N-benzyl-3-(3,4-dichlorophenyl)-3-morpholinyl-propylamine (VI5)

3-chloro-1-(3,4-dichlorophenyl)-acetone (0.05 mol), N-methylbenzylamine hydrochloride (0.05 mol) and diisopropyl ethylamine (0.15 mol) are dissolved in acetonitrile (100 mL). Following procedures described in General Method Two-Method B, a white solid product is obtained (16.7 g). The yield is 85.0%. MS(m/z): 322.1 [M+1]$^+$.

The product obtained above (10 mmol) and $NaBH_4$ (10 mmol) are dissolved in methanol (50 mL). Following procedures described in General Method Three, a white solid is obtained (3.64 g). The yield is 92.2%. MS(m/z): 324.1 [M+1]$^+$.

The product obtained from the previous step (8 mmol), triethylamine (9.6 mmol) and p-methyl benzenesulfonyl chloride (8.8 mmol) are dissolved in acetonitrile (30 mL). Following procedures described in General Method Four, morpholine (24 mmol) and $K_2CO_3$ (8 mmol) are added. The hydrochloride of N-methyl-N-benzyl-3-(3,4-dichlorophenyl)-3-morpholinyl-propylamine (VI-5) is obtained as a white solid (1.8 g). The yield is 48.5%. Mp=257.0-259.5° C., MS(m/z): 393.3 [M+1]$^+$.

$^1$H NMR (DMSO-$d_6$) +$D_2O$: δ: 2.45-2.58 (m, 2H, —$CH_2CH_2N$—), 2.49-2.58 (m, 2H, —$NCH_2CH_2O$), 2.69 (s, 3H, —$NCH_3$), 2.87-2.95 (m, 2H, —$CH_2CH_2N$—), 3.08-3.15 (m, 2H, —$NCH_2CH_2O$), 3.73-3.79 (m, 4H, —$NCH_2CH_2O$), 4.24 (s, 2H, Ar—$CH_2$—), 4.31-4.33 (d, J=6.4 Hz, 1H, Ar—CH—), 7.36-7.48 (m, 6H, Ar—H), 7.66-7.68 (d, J=8.4 Hz, 1H, Ar—H), 7.77 (d, J=2.0 Hz, 1H, Ar—H).

Example 6

Preparation of the hydrochloride of 4-(3-(3,4-dichlorophenyl)-3-(pyrrolidin-1-yl)propylmorpholine (VI-6)

3-chloro-1-(3,4-dichlorophenyl)-acetone (0.05 mol), morpholine (0.05 mol) and diisopropyl ethylamine (0.15 mol) are dissolved in acetonitrile (100 mL). Following procedures described in General Method Two-Method B, a white solid product is obtained (13.2 g). The yield is 81.7%. MS(m/z): 288.1 [M+1]⁺.

The product obtained above (10 mmol) and NaBH₄ (10 mmol) are dissolved in methanol (50 mL). Following procedures described in General Method Three, a white solid is obtained (3.04 g). The yield is 93.5%. MS(m/z): 290.2 [M+1]⁺.

The product obtained above (8 mmol), triethylamine (9.6 mmol) and p-methyl benzenesulfonyl chloride (8.8 mmol) are dissolved in acetonitrile (30 mL). Following procedures described in General Method Four, tetrahydropyrrole (24 mmol) and K₂CO₃ (8 mmol) are added. The hydrochloride of 4-(3-(3,4-dichlorophenyl)-3-(pyrrolidin-1-yl) propylmorpholine (VI-6) is obtained as a white solid (1.6 g). The yield is 48.3%. Mp=205.0-207.5° C., MS(m/z): 343.3 [M+1]⁺.

¹H NMR (DMSO-d₆)+D₂O: δ:1.92 (m, 4H, —NCH₂CH₂CH₂CH₂N—), 2.60 (m, 2H, —CH₂CH₂N—), 2.91-2.94 (m, 2H, —CH₂CH₂N—), 3.07 (m, 4H, —NCH₂CH₂CH₂CH₂N—), 3.07 (m, 4H, —NCH₂CH₂O), 3.78 (m, 4H, —NCH₂CH₂O), 4.43-4.46 (d, J=10.8 Hz, 1H, Ar—CH—), 7.61-7.63 (d, J=8.4 Hz, 1H, Ar—H—), 7.71-7.73 (d, J=8.4 Hz, 1H, Ar—H), 7.93 (s, 1H, Ar—H).

Example 7

Preparation of the hydrochloride of N,N-dimethyl-3-(3,4-dichlorophenyl)-3-piperidyl-propylamine (VI-7)

The hydrochloride of N,N-dimethyl-3-(3,4-dichlorophenyl)-3-hydroxy-propylamine (8 mmol), triethylamine (9.6 mmol) and p-methyl benzenesulfonyl chloride (8.8 mmol) are dissolved in acetonitrile (30 mL). Following procedures described in General Method Four, piperidine (24 mmol) and K₂CO₃ (8 mmol) are added. The hydrochloride of N,N-dimethyl-3-(3,4-dichlorophenyl)-3-piperidyl-propylamine (VI-7) is obtained according to General Method Four as a white solid (1.60 g). The yield is 51.8%. Mp=169.1-171.8° C., MS(m/z): 315.3 [M+1]⁺.

¹H NMR (DMSO-d₆)+D₂O: δ: 1.65-1.70 (m, 6H, —NCH₂CH₂CH₂CH₂CH₂N—), 2.09-2.12 (m, 2H, —CH₂CH₂N—), 2.69 (s, 6H, N(CH₃)₂), 2.95-3.00 (m, 2H, —CH₂CH₂N—), 3.17 (m, 4H, —NCH₂CH₂CH₂CH₂CH₂N—), 4.95-4.98 (d, J=9.6 Hz, 1 H, Ar—CH—), 7.26-7.29 (dd, J₁=2.0 Hz, J₂=8.0 Hz, 1H, Ar—H), 7.53-7.54 (d, J=1.2 Hz, 1H, Ar—H), 7.61-7.64 (d, J=8.4 Hz, 1H, Ar—H).

Example 8

Preparation of the hydrochloride of N,N-dimethyl-3-(4-chlorophenyl)-3-morpholinyl-propylamine (VI-8)

4-chloroacetophenone (0.1 mol), dimethylamine hydrochloride (0.11 mol) and polyformaldehyde (0.13 mol) are dissolved in 95% ethanol (20 mL) and added with concentrated HCl (0.2 mL). Following procedures described in General Method Two-Method C, a white solid is obtained (19.8 g). The yield is 80.2%. MS(m/z): 212.1 [M+1]⁺.

The product obtained above (10 mmol) and NaBH₄ (10 mmol) are dissolved in methanol (50 mL). Following procedures described in General Method Three, a white solid is obtained (2.32 g). The yield is 93.2%. MS(m/z): 214.1 [M+1]⁺.

The intermediate obtained above (8 mmol), triethylamine (9.6 mmol) and p-methyl benzenesulfonyl chloride (8.8 mmol) are dissolved in acetonitrile (30 mL). Following procedures described in General Method Four, morpholine (24 mmol) and K₂CO₃ (8 mmol) are added. The hydrochloride of N,N-dimethyl-3-(4-chlorophenyl)-3-morpholinyl-propylamine (VI-8) is obtained as a white solid (1.43 g). The yield is 50.5%. Mp=131.0-134.3° C., MS(m/z): 283.2 [M+1]⁺.

¹H NMR (DMSO-d₆): δ: 2.01-2.06 (m, 1H, —CH₂CH₂N—), 2.29-2.37 (m, 4H, —NCH₂CH₂O), 2.39-2.42 (m, 1H, —CH₂CH₂N—), 2.69 (s, 6H, N(CH₃)₂), 2.79-2.86 (m, 1H, —CH₂CH₂N—), 3.01-3.08 (m, 1H, —CH₂CH₂N—), 3.51-3.55 (m, 4H, —NCH₂CH₂O), 3.57-3.60 (t, J=7.2 Hz, 1H, Ar—CH—), 7.28-7.30 (d, J=8.4 Hz, 2H, Ar—H), 7.41-7.43 (d, J=8.0 Hz, 2H, Ar—H), 10.99 (br, 1H, HCl, +D₂O vanished).

Example 9

Preparation of the hydrochloride of 4-(3-(4-chlorophenyl)-3-(pyrrolidin-1-yl)propylmorpholine (VI-9)

4-chloroacetophenone (20 mmol), morpholine (22 mmol) and polyformaldehyde (26 mmol) are dissolved in 95% ethanol (10 mL) and added with concentrated HCl (0.05 mL) Following procedures described in General Method Two-Method C, a white solid is obtained (5.2 g). The yield is 90.0%. MS(m/z): 254.2 [M+1]⁺.

The product obtained above (10 mmol) and NaBH₄ (10 mmol) are dissolved in methanol (50 mL) Following procedures described in General Method Three, a white solid is obtained (2.6 g). The yield is 89.3%. MS(m/z): 256.2 [M+1]⁺.

The product from the previous step (8 mmol), triethylamine (9.6 mmol) and p-methyl benzenesulfonyl chloride (8.8 mmol) are dissolved in acetonitrile (30 mL). Following procedures described in General Method Four, tetrahydropyrrole (24 mmol) and K₂CO₃ (8 mmol) are added. The hydrochloride of 4-(3-(4-chlorophenyl)-3-(pyrrolidin-1-yl)propylmorpholine (VI-9) is obtained according to General Method Four as a white solid (1.56 g). The yield is 51.3%. Mp=202.5-203.7° C., MS(m/z): 309.3 [M+1]⁺.

¹H NMR (DMSO-d₆)+D₂O: δ:1.93 (m, 4H, —NCH₂CH₂CH₂CH₂N—), 2.61 (m, 2H, —CH₂CH₂N—), 2.90-2.94 (m, 2H, —CH₂CH₂N—), 3.06 (m, 4H, —NCH₂CH₂CH₂CH₂N—), 3.07 (m, 4H, —NCH₂CH₂O), 3.81 (m, 4H, —NCH₂CH₂O), 4.43-4.46 (d, J=10.8 Hz, 1H, Ar—CH), 7.22-7.25 (d, J=8.4 Hz, 2H, Ar—H), 7.40-7.42 (d, J=8.0 Hz, 2H, Ar—H).

Example 10

Preparation of the hydrochloride of N,N-dimethyl-3-(4-methylphenyl)-3-morpholinyl-propylamine (VI-10)

4-methylacetophenone (20 mmol), dimethylamine hydrochloride (22 mmol) and polyformaldehyde (26 mmol) are dissolved in 95% ethanol (10 mL) and added with concentrated HCl (0.05 mL). Following procedures described in General Method Two-Method C, a white solid is obtained (3.76 g). The yield is 82.9%. MS(m/z): 192.1 [M+1]⁺.

The product obtained above (10 mmol) and NaSH₄ (10 mmol) are dissolved in methanol (50 mL). Following procedures described in General Method Three, a white solid is obtained (2.06 g). The yield is 90.2%. MS(m/z): 194.1 [M+1]⁺.

The product from the previous step (8 mmol), triethylamine (9.6 mmol) and p-methyl benzenesulfonyl chloride (8.8 mmol) are dissolved in acetonitrile (30 mL). Following procedures described in General Method Four, morpholine (24 mmol) and $K_2CO_3$ (8 mmol) are added. The hydrochloride of N,N-dimethyl-3-(4-methylphenyl)-3-morpholinylpropylamine (VI-10) is obtained according to General Method Four as a white solid (1.34 g). The yield is 50.0%. Mp=234.1-236.9° C., MS(m/z): 263.2 [M+1]$^+$.

$^1$H NMR (DMSO-d$_6$): δ: 2.35 (s, 3H, Ar—CH$_3$), 2.62-2.64 (t, J=6.4 Hz, 2H, —CH$_2$CH$_2$N—), 2.70 (s, 6H, N(CH$_3$)$_2$), 2.80-2.82 (t, J=6.4 Hz, 2H, —CH$_2$CH$_2$N—), 2.87-2.94 (m, 4H, —NCH$_2$CH$_2$O), 3.66-3.87 (m, 4H, —NCH$_2$CH$_2$O), 4.51-4.53 (d, J=8.0 Hz, 1H, Ar—CH—), 7.30-7.32 (d, J=8.0 Hz, 2H, Ar—H), 7.57-7.59 (d, J=8.0 Hz, 2H, Ar—H), 10.99 (br, 1H, HCl, +D$_2$O vanished), 12.18 (br, 1H, HCl, +D$_2$O vanished).

Example 11

Preparation of the hydrochloride of 4-(3-(4-methylpiperazin-1-yl)-1-(4-methylphenyl)propylmorpholine (VI-11)

4-methylacetophenone (20 mmol), 1-methylpiperazine hydrochloride (22 mmol) and polyformaldehyde (26 mmol) are dissolved in 95% ethanol (10 mL) and added with concentrated HCl (0.05 mL). Following procedures described in General Method Two-Method C, a white solid is obtained (4.50 g). The yield is 79.8%. MS(m/z): 247.1 [M+1]$^+$.

The intermediate obtained above (10 mmol) and NaBH$_4$ (10 mmol) are dissolved in methanol (50 mL). Following procedures described in General Method Three, a white solid is obtained (2.68 g). The yield is 94.4%. MS(m/z): 279.2 [M+1]$^+$.

The product from the previous step (8 mmol), triethylamine (9.6 mmol) and p-methyl benzenesulfonyl chloride (8.8 mmol) are dissolved in acetonitrile (30 mL). Following procedures described in General Method Four, morpholine (24 mmol) and $K_2CO_3$ (8 mmol) are added. The hydrochloride of 4-(3-(4-methylpiperazin-1-yl)-1-(4-methylphenyl)propylmorpholine (VI-11) is obtained according to General Method Four as a white solid (1.43 g). The yield is 46.0%. MS(m/z): 318.2 [M+1]$^+$.

$^1$H NMR (DMSO-d$_6$): δ: 2.02-2.05 (m, 2H, —CHCH$_2$CH$_2$N—), 2.20 (s, 3H, —NCH$_3$), 2.33 (m, 8H, —NCH$_2$CH$_2$N—), 2.35 (s, 3H, Ar—CH$_3$), 2.82-2.89 (m, 2H, —CHCH$_2$CH$_2$N—), 3.08-3.16 (m, 2H, —NCH$_2$CH$_2$O), 3.63-3.75 (m, 4H, —NCH$_2$CH$_2$O), 4.28 (s, 2H, Ar—CH$_2$—), 4.33-4.35 (t, J=7.2 Hz, 1H, Ar—CH—), 7.31-7.45 (m, 7H, Ar—H), 7.73 (d, J=2.0 Hz, 1H, Ar—H), 10.98 (br, 1H, HCl, +D$_2$O vanished).

Example 12

Preparation of the hydrochloride of 4-(3-(4-methylphenyl)-3-(morpholinyl)propylpyrrole (VI-12)

4-methylacetophenone (20 mmol), pyrrolidine (22 mmol) and polyformaldehyde (26 mmol) are dissolved in 95% ethanol (10 mL) and added with concentrated HCl (0.05 mL) Following procedures described in General Method Two-Method C, a white solid is obtained (4.40 g). The yield is 87.0%. MS(m/z): 218.1 [M+1]$^+$.

The intermediate obtained above (10 mmol) and NaBH$_4$ (10 mmol) are dissolved in methanol (50 mL). Following procedures described in General Method Three, a white solid is obtained (2.25 g). The yield is 88.2%. MS(m/z): 220.2 [M+1]$^+$.

The product from the previous step (8 mmol), triethylamine (9.6 mmol) and p-methyl benzenesulfonyl chloride (8.8 mmol) are dissolved in acetonitrile (30 mL). Following procedures described in General Method Four, morpholine (24 mmol) and $K_2CO_3$ (8 mmol) are added. The hydrochloride of 4-(3-(4-methylphenyl)-3-(morpholinyl)propylpyrrole (VI-12) is obtained according to General Method Four as a white solid (1.45 g). The yield is 50.3%. MS(m/z): 289.2 [M+1]$^+$.

$^1$H NMR (DMSO-d$_6$)+D$_2$O: δ: 1.89 (m, 4H, —NCH$_2$CH$_2$CH$_2$CH$_2$N—), 2.62-2.70 (m, 2H, —CHCH$_2$CH$_2$N—), 2.35 (s, 3H, Ar—CH$_3$), 3.13 (m, 4H, —NCH$_2$CH$_2$CH$_2$CH$_2$N—), 3.15 (m, 2H, —CHCH$_2$CH$_2$N—), 3.30-2.41 (m, 4H, —NCH$_2$CH$_2$O), 3.56-3.65 (m, 4H, —NCH$_2$CH$_2$O), 3.77-3.79 (t, J=7.2 Hz, 1H, Ar—CH—), 7.35-7.38 (d, J=8.0 Hz, 2H, Ar—H), 7.42-7.44 (d, J=8.0 Hz, 2H, Ar—H).

Example 13

Preparation of the hydrochloride of N,N-dimethyl-3-(benzothiophen-3-yl)-3-(pyrrolidin-1-yl)-propylamine (VI-13)

To the solution of benzothiophene (0.05 mol) dissolved in dichloromethane (30 mL), AlCl$_3$ (0.10 mol) is added batch by batch and 3-chloropropionyl chloride (0.055 mol) is added dropwise, while the internal temperature is maintained below 5° C. Following procedures described in General Method One—Method A, 3-chloro-1-(benzothiophen-3- yl)-acetone is obtained as a white solid (9.6 g). The yield is 85.3%. MS(m/z): 225.0 [M+1]$^+$.

This intermediate (0.03 mol) and dimethylamine aqueous solution (0.15 mol) are dissolved in anhydrous ethanol (50 mL). Following procedures described in General Method Two-Method A, a white solid product is obtained (6.5 g). The yield is 80.3%. MS(m/z): 234.1 [M+1]$^+$.

The product obtained above (10 mmol) and NaBH$_4$ (10 mmol) are dissolved in methanol (50 mL) Following procedures described in General Method Three, a white solid is obtained (2.45 g). The yield is 90.5%. MS(m/z): 236.2 [M+1]$^+$.

The product from the previous step (8 mmol), triethylamine (9.6 mmol) and p-methyl benzenesulfonyl chloride (8.8 mmol) are dissolved in acetonitrile (30 mL). Following procedures described in General Method Four, tetrahydropyrrole (24 mmol) and $K_2CO_3$ (8 mmol) are added. The hydrochloride of N,N-dimethyl-3-(benzothiophen-3-yl)-3-(pyrrolidin-1-yl)-propylamine (VI-13) is obtained according to General Method Four as a white solid (1.24 g). The yield is 43.2%. Mp=259.7-262.2° C., MS(m/z): 289.3 [M+1]$^+$.

$^1$H NMR (DMSO-d$_6$)+D$_2$O: δ: 1.91 (m, 4H, —NCH$_2$CH$_2$CH$_2$CH$_2$N—), 2.62-2.70 (m, 2H, —CH$_2$CH$_2$N—), 2.73 (s, 6H, N(CH$_3$)$_2$), 2.97-3.02 (m, 2H, —CH$_2$CH$_2$N—), 3.12 (m, 4H, —NCH$_2$CH$_2$CH$_2$CH$_2$N—), 4.98-5.01 (d, J=9.6 Hz, 1H, Ar—CH—), 7.44-7.52 (m, 2H, Ar—H), 8.05-8.08 (t, J=8.4 Hz, 2H, Ar—H), 8.22 (s, 1H, Ar—H).

Example 14

Preparation of the hydrochloride of N-methyl-N-benzyl-3-(benzothiophen-3-yl)-3-(pyrrolidin-1-yl)-propylamine (VI-14)

3-chloro-1-(benzothiophen-3-yl)-acetone (0.05 mol), N-methylbenzylamine hydrochloride (0.05 mol) and diisopropyl ethylamine (0.15 mol) are dissolved in acetonitrile (100 mL). Following procedures described in General Method Two-Method B, a white solid product is obtained (14.4 g). The yield is 83.5%. MS(m/z): 310.2 [M+1]$^+$.

The intermediate obtained above (10 mmol) and NaBH$_4$ (10 mmol) are dissolved in methanol (50 mL). Following procedures described in General Method Three, a white solid is obtained (3.12 g). The yield is 90.0%. MS(m/z): 312.2 [M+1]$^+$.

The product from the previous step (8 mmol), triethylamine (9.6 mmol) and p-methyl benzenesulfonyl chloride (8.8 mmol) are dissolved in acetonitrile (30 mL). Following procedures described in General Method Four, tetrahydropyrrole (24 mmol) and K$_2$CO$_3$ (8 mmol) are added. The hydrochloride of N-methyl-N-benzyl-3-(benzothiophen-3-yl)-3-(pyrrolidin-1-yl)-propylamine (VI-14) is obtained according to General Method Four as a white solid (1.83 g). The yield is 52.5%. Mp=297.0-299.5° C., MS(m/z): 365.3 [M+1]$^+$.

$^1$H NMR (DMSO-d$_6$) +D$_2$O: δ: 1.93 (m, 4H, —NCH$_2$CH$_2$CH$_2$N—), 2.58-2.68 (m, 2H, —CH$_2$CH$_2$N—), 2.73 (s, 3H, —NCH$_3$), 2.92-2.97 (m, 2H, —CH$_2$CH$_2$N—), 3.15 (m, 4H, —NCH$_2$CH$_2$CH$_2$N—), 4.25 (s, 2H, Ar—CH$_2$—), 4.58-4.60 (d, J=7.6 Hz, 1H, Ar—CH—), 7.33-7.42 (m, 5H, Ar—H), 7.44-7.53 (m, 2H, Ar—H), 8.06-8.09 (t, J=8.4 Hz, 2H, Ar—H), 8.24 (s, 1H, Ar—H).

Example 15

Preparation of the hydrochloride of N-methyl-3-(benzothiophen-3-yl)-3-(pyrrolidin-1-yl)-propylamine (VI-15)

A hydrogenation reaction at normal temperature and pressure is performed in the solution of N-methyl-N-benzyl-3-(benzothiophen-3-yl)-3-(pyrrolidin-1-yl)-propylamine hydrochloride (5 mmol) in methanol (30 mL) with 5% Pd/C (0.2 g) for 2 h. After the reaction, the Pd/C is removed through filtration and the filtrate is concentrated to give a white solid. Recrystalization of the white solid with anhydrous ethanol (10 mL) yields the hydrochloride of N-methyl-3-(benzothiophen-3-yl)-3-(pyrrolidin-1-yl)-propylamine (VI-15) (1.18 g). The yield is 68.4%. Mp=189.3-192.0° C., MS(m/z): 275.2 [M+1]$^+$.

$^1$H NMR (DMSO-d$_6$)+D$_2$O: δ: 1.85 (m, 4H, —NCH$_2$CH$_2$CH$_2$N—), 2.58-2.67 (m, 2H, —CH$_2$CH$_2$N—), 2.95-3.00 (m, 2H, —CH$_2$CH$_2$N—), 3.15 (m, 4H, —NCH$_2$CH$_2$CH$_2$N—), 3.45 (s, 3H, N—CH$_3$), 4.97-5.00 (d, J=9.6 Hz, 1H, Ar—CH—), 7.42-7.48 (m, 2H, Ar—H), 8.02-8.05 (t, J=8.4 Hz, 2H, Ar—H), 8.25 (s, 1H, Ar—H).

Example 16

Preparation of the hydrochloride of N,N-dimethyl-3-(benzothiophen-3-yl)-3-piperidyl-propylamine (VI-16)

N,N-dimethyl-3-(benzothiophen-3-yl)-3-hydroxy-propylamine hydrochloride (8 mmol), triethylamine (9.6 mmol) and p-methyl benzenesulfonyl chloride (8.8 mmol) are dissolved in acetonitrile (30 mL). Following procedures described in General Method Four, piperidine (24 mmol) and K$_2$CO$_3$ (8 mmol) are added. The hydrochloride of N,N-dimethyl-3-(benzothiophen-3-yl)-3-piperidyl-propylamine (VI-16) is obtained according to General Method Four as a white solid (1.65 g). The yield is 55.3%. Mp=265.3-267.0° C., MS(m/z): 303.3 [M+1]$^+$.

$^1$H NMR (DMSO-d$_6$)+D$_2$O: δ: 1.65-1.72 (m, 6H, —NCH$_2$CH$_2$CH$_2$CH$_2$CH$_2$N—), 2.08-2.12 (m, 2H, —CH$_2$CH$_2$N—), 2.69 (s, 6H, N(CH$_3$)$_2$), 2.95-3.00 (m, 2H, —CH$_2$CH$_2$N—), 3.15 (m, 4H, —NCH$_2$CH$_2$CH$_2$CH$_2$CH$_2$N—), 4.95-4.98 (d, J=9.6 Hz, 1H, Ar—CH—), 7.42-7.48 (m, 2H, Ar—H), 8.03-8.05 (t, J=8.4 Hz, 2H, Ar—H), 8.24 (s, 1H, Ar—H).

Example 17

Preparation of the hydrochloride of N-methyl-N-benzyl-3-(benzothiophen-3-yl)-3-piperidyl-propylamine (VI-17)

N-methyl-N-benzyl-3-(benzothiophen-3-yl)-3-hydroxy-propylamine hydrochloride (8 mmol), triethylamine (9.6 mmol) and p-methyl benzenesulfonyl chloride (8.8 mmol) are dissolved in acetonitrile (30 mL). Following procedures described in General Method Four, piperidine (24 mmol) and K$_2$CO$_3$ (8 mmol) are added. The hydrochloride of N-methyl-N-benzyl-3-(benzothiophen-3-yl)-3-piperidyl-propylamine (VI-17) is obtained according to General Method Four as a white solid (2.07 g). The yield is 57.4%. Mp=312.0-313.5° C., MS(m/z): 379.3 [M+1]$^+$.

$^1$H NMR (DMSO-d$_6$)+D$_2$O: δ: 1.66-1.74 (m, 6H, —NCH$_2$CH$_2$CH$_2$CH$_2$N—), 2.13-2.18 (m, 2H, —CH$_2$CH$_2$N—), 2.70 (s, 3H, —NCH$_3$), 2.95-3.02 (m, 2H, —CH$_2$CH$_2$N—), 3.17 (m, 4H, —NCH$_2$CH$_2$CH$_2$CH$_2$N—), 4.26 (s, 2H, Ar—CH$_2$—), 4.58-4.60 (d, J=6.4 Hz, 1H, Ar—CH—), 7.30-7.41 (m, 5H, Ar—H), 7.42-7.51 (m, 2H, Ar—H), 8.07-8.10 (t, J=8.4 Hz, 2H, Ar—H), 8.27 (s, 1H, Ar—H).

Example 18

Preparation of the hydrochloride of N-methyl-3-(benzothiophen-3-yl)-3-piperidyl-propylamine (VI-18)

A hydrogenation reaction at normal temperature and pressure is performed in the solution of N-methyl-N-benzyl-3-(benzothiophen-3-yl)-3-piperidyl-propylamine hydrochloride (5 mmol) in methanol (30 mL) with 5% Pd/C (0.2 g) for 2 h. After the reaction, the Pd/C is removed through filtration and the filtrate is concentrated to give a white solid. Recrystalization of the white solid with anhydrous ethanol (10 mL) yields the hydrochloride of N-methyl-3-(benzothiophen-3-yl)-3-piperidyl-propyl amine (VI-18) (1.26 g). The yield is 70.0%. Mp=193.2-195.0° C., MS(m/z): 289.1 [M+1]$^+$.

$^1$H NMR (DMSO-d$_6$)+D$_2$O: δ: 1.60-1.72 (m, 6H, —NCH$_2$CH$_2$CH$_2$CH$_2$N—), 2.56-2.62 (m, 2H, —CH$_2$CH$_2$N—), 2.97-3.02 (m, 2H, —CH$_2$CH$_2$N—), 3.16 (m, 4H, —NCH$_2$CH$_2$CH$_2$CH$_2$N—), 3.46 (s, 3H, N—CH$_3$), 4.92-4.95 (d, J=9.6 Hz, 1H, Ar—CH—), 7.40-7.46 (m, 2H, Ar—H), 8.00-8.03 (t, J=8.4 Hz, 2H, Ar—H), 8.23 (s, 1H, Ar—H).

Example 19

Preparation of the hydrochloride of N,N-dimethyl-3-(benzothiophen-2-yl)-3-(pyrrolidin-1-yl)-propylamine (VI-19)

2-acetylbenzothiophene (20 mmol), dimethylamine hydrochloride (22 mmol) and polyformaldehyde (26 mmol)

are dissolved in 95% ethanol (10 mL) and added with concentrated HCl (0.05 mL). Following procedures described in General Method Two-Method C, a white solid is obtained (4.34 g). The yield is 80.6%. MS(m/z): 234.1 [M+1]$^+$.

The intermediate obtained above (10 mmol) and NaBH$_4$ (10 mmol) are dissolved in methanol (50 mL). Following procedures described in General Method. Three, a white solid is obtained (2.57 g). The yield is 95.0%. MS (m/z): 236.1 [M+1]$^+$.

The product from the previous step (8 mmol), triethylamine (9.6 mmol) and p-methyl benzenesulfonyl chloride (8.8 mmol) are dissolved in acetonitrile (30 mL). Following procedures described in General Method Four, tetrahydropyrrole (24 mmol) and K$_2$CO$_3$ (8 mmol) are added. The hydrochloride of N,N-dimethyl-3-(benzothiophen-2-yl)-3-(pyrrolidin-1-yl)-propylamine (VI-19) is obtained according to General Method Four as a white solid (1.31 g). The yield is 45.6%. Mp=255.0-257.2° C., MS(m/z): 289.2 [M+1]$^+$.

$^1$H NMR (DMSO-d$_6$)+D$_2$O: δ: 1.93 (m, 4H, —NCH$_2$CH$_2$CH$_2$N—), 2.52-2.60 (m, 2H, —CH$_2$CH$_2$N—), 2.75 (s, 6H, —NCH$_3$), 2.76 (m, 2H, —NCH$_2$CH$_2$CH$_2$N—), 3.05-3.11 (m, 2H, —CH$_2$CH$_2$N—), 3.20 (m, 2H, —NCH$_2$CH$_2$CH$_2$N—), 4.96-5.00 (dd, J$_1$=3.2 Hz, J$_1$=11.2 Hz, 1H, Ar—CH—), 7.41-7.45 (m, 2H, Ar—H), 7.79 (s, 1H, Ar—H), 7.88-7.90 (m, 1H, Ar—H), 7.99-8.02 (m, 1H, Ar—H).

Example 20

Preparation of the hydrochloride of N-methyl-N-benzyl-3-(benzothiophen-2-yl)-3-(pyrrolidin-1-yl)-propylamine (VI-20)

2-acetylbenzothiophene (20 mmol), N-methylbenzylamine hydrochloride (22 mmol) and polyformaldehyde (26 mmol) are dissolved in 95% ethanol (10 mL) and added with concentrated HCl (0.05 mL). Following procedures described in General Method Two-Method C, a white solid is obtained (5.33 g). The yield is 70.0%. MS(m/z): 310.1 [M+1]$^+$.

The intermediate obtained above (10 mmol) and NaBH$_4$ (10 mmol) are dissolved in methanol (50 mL). Following procedures described in General Method Three, a white solid is obtained (3.52 g). The yield is 92.0%. MS(m/z): 312.1 [M+1]$^+$.

The product from the previous step (8 mmol), triethylamine (9.6 mmol) and p-methyl benzenesulfonyl chloride (8.8 mmol) are dissolved in acetonitrile (30 mL). Following procedures described in General Method Four, tetrahydropyrrole (24 mmol) and K$_2$CO$_3$ (8 mmol) are added. The hydrochloride of N-methyl-N-benzyl-3-(benzothiophen-2-yl)-3-(pyrrolidin-1-yl)yl-propylamine (VI20) is obtained according to General Method Four as a white solid (1.40 g). The yield is 40.0%. Mp=287.5-289.2° C., MS(m/z): 365.3 [M+1]$^+$.

$^1$H NMR (DMSO-d$_6$) +D$_2$O: δ: 1.90 (m, 4H, —NCH$_2$CH$_2$CH$_2$N—), 2.56-2.64 (m, 2H, —CH$_2$CH$_2$N—), 2.71 (s, 3H, —NCH$_3$), 2.90-2.95 (m, 2H, —CH$_2$CH$_2$N—), 3.14 (m, 4H, —NCH$_2$CH$_2$CH$_2$N—), 4.23 (s, 2H, Ar—CH$_2$—), 4.56-4.58 (d, J=6.4 Hz, 1H, Ar—CH—), 7.25-7.32 (m, 5H, Ar—H), 7.36 (s, 1H, Ar—H), 7.45-7.54 (m, 2H, Ar—H), 8.07-8.10 (t, J=8.4 Hz, 2H, Ar—H).

Example 21

Preparation of the hydrochloride of N-methyl-3-(benzothiophen-2-yl)-3-(pyrrolidin-1-yl)-propylamine (VI-21)

A hydrogenation reaction at normal temperature and pressure is performed in the solution of N-methyl-N-benzyl-3-(benzothiophen-2-yl)-3-(pyrrolidin-1-yl)-propylamine hydrochloride (5 mmol) in methanol (30 mL) with 5% Pd/C (0.2 g) for 2 h. After the reaction, the Pd/C is removed through filtration and the filtrate is concentrated to give a white solid. Recrystalization of the white solid with anhydrous ethanol (10 mL) yields the hydrochloride of N-methyl-3-(benzothiophen-2-yl)-3-(pyrrolidin-1-yl)-propylamine (VI-21) (1.05 g). The yield is 60.5%. Mp=175.0-176.8° C., MS(m/z): 275.3 [M+1]$^+$.

$^1$H NMR (DMSO-d$_6$)+D$_2$O: δ: 1.83-1.85 (m, 4H, —NCH$_2$CH$_2$CH$_2$N—), 2.62-2.69 (m, 2H, —CH$_2$CH$_2$N—), 2.96-3.02 (m, 2H, —CH$_2$CH$_2$N—), 3.15-3.19 (m, 4H, —NCH$_2$CH$_2$CH$_2$N—), 3.43 (s, 3H, N—CH$_3$), 4.98-5.00 (d, J=9.6 Hz, 1H, Ar—CH—), 7.25 (s, 1H, Ar—H), 7.45-7.49 (m, 2H, Ar—H), 7.95-7.97 (t, J=8.4 Hz, 2H, Ar—H).

Example 22

Preparation of the hydrochloride of N,N-dimethyl-3-(benzothiophen-2-yl)-3-piperidinyl-propylamine (VI-22)

N,N-dimethyl-3-(benzothiophen-2-yl)-3-hydroxy-propylamine hydrochloride (8 mmol), triethylamine (9.6 mmol) and p-methyl benzenesulfonyl chloride (8.8 mmol) are dissolved in acetonitrile (30 mL). Following procedures described in General Method Four, piperidine (24 mmol) and K$_2$CO$_3$ (8 mmol) are added. The hydrochloride of N,N-dimethyl-3-(benzothiophen-2-yl)-3-piperidinyl-propylamine (VI-22) is obtained according to General Method Four as a white solid (1.50 g). The yield is 50.2%. Mp=256.2-258.0° C., MS(m/z): 303.2 [M+1]$^+$.

$^1$H NMR (DMSO-d$_6$)+D$_2$O: δ: 1.58-1.65 (m, 6H, —NCH$_2$CH$_2$CH$_2$CH$_2$N—), 2.02-2.09 (m, 2H, —CH$_2$CH$_2$N—), 2.72 (s, 6H, N(CH$_3$)$_2$), 2.95-3.02 (m, 2H, —CH$_2$CH$_2$N—), 3.13-3.16 (m, 4H, —NCH$_2$CH$_2$CH$_2$CH$_2$N—), 4.96-4.99 (d, J=9.6 Hz, 1H, Ar—CH—), 7.23 (s, 1H, Ar—H), 7.42-7.48 (m, 2H, Ar—H), 8.03-8.05 (t, J=8.4 Hz, 2H, Ar—H).

Example 23

Preparation of the hydrochloride of N-methyl-N-benzyl-3-(benzothiophen-2-yl)-3-piperidyl-propylamine (VI-23)

N-methyl-N-benzyl-3-(benzothiophen-2-yl)-3-hydroxypropylamine hydrochloride (8 mmol), triethylamine (9.6 mmol) and p-methyl benzenesulfonyl chloride (8.8 mmol) are dissolved in acetonitrile (30 mL). Following procedures described in General Method Four, piperidine (24 mmol) and K$_2$CO$_3$ (8 mmol) are added. The hydrochloride of N-methyl-N-benzyl-3-(benzothiophen-2-yl)-3-piperidyl-propylamine (VI-23) is obtained according to General Method Four as a white solid (1.65 g). The yield is 45.9%. Mp=298.5-300.0° C., MS(m/z): 379.2 [M+1]$^+$.

$^1$H NMR (DMSO-d$_6$)+D$_2$O: δ: 1.62-1.70 (m, 6H, —NCH$_2$CH$_2$CH$_2$CH$_2$N—), 2.15-2.19 (m, 2H,

—CH$_2$CH$_2$N—), 2.71 (s, 3H, —NCH$_3$), 2.98-3.04 (m, 2H, —CH$_2$CH$_2$N—), 3.13-3.16 (m, 4H, —NCH$_2$CH$_2$CH$_2$CH$_2$N—), 4.27 (s, 2H, Ar—CH$_2$—), 4.58-4.60 (d, J=6.4 Hz, 1H, Ar—CH—), 7.25 (s, 1H, Ar—H), 7.30-7.41 (m, 5H, Ar—H), 7.42-7.51 (m, 2H, Ar—H), 8.07-8.10 (t, J=8.4 Hz, 2H, Ar—H).

Example 24

Preparation of the hydrochloride of N-methyl-3-(benzothiophen-2-yl)-3-piperidyl-propylamine (VI-24)

A hydrogenation reaction at normal temperature and pressure is performed in the solution of N-methyl-N-benzyl-3-(benzothiophen-2-yl)-3-piperidyl-propylamine hydrochloride (5 mmol) in methanol (30 mL) with 5% Pd/C (0.2 g) for 2 h. After the reaction, the Pd/C is removed through filtration and the filtrate is concentrated to give a white solid. Recrystalization of the white solid with anhydrous ethanol (10 mL) yields the hydrochloride of N-methyl-3-(benzothiophen-2-yl)-3-piperidyl-propylamine (VI-24) (1.27 g). The yield is 70.5%. Mp=185.3-187.0° C., MS(m/z): 289.0 [M+1]$^+$.

$^1$H NMR (DMSO-d$_6$)+D$_2$O: δ: 1.62-1.73 (m, 6H, —NCH$_2$CH$_2$CH$_2$CH$_2$N—), 2.54-2.59 (m, 2H, —CH$_2$CH$_2$N—), 2.97-3.03 (m, 2H, —CH$_2$CH$_2$N—), 3.16-3.19 (m, 4H, —NCH$_2$CH$_2$CH$_2$CH$_2$N—), 3.47 (s, 3H, N—CH$_3$), 4.92-4.94 (d, J=9.6 Hz, 1H, Ar—CH—), 7.25 (s, 1H, Ar—H), 7.42-7.45 (m, 2H, Ar—H), 8.03-8.06 (t, J=8.4 Hz, 2H, Ar—H).

Example 25

Preparation of the hydrochloride of N,N-dimethyl-3-(benzothiophen-2-yl)-3-morpholinyl-propylamine (VI-25)

N,N-dimethyl-3-(benzothiophen-2-yl)-3-hydroxy-propylamine hydrochloride (8 mmol), triethylamine (9.6 mmol) and p-methyl benzenesulfonyl chloride (8.8 mmol) are dissolved in acetonitrile (30 mL). Following procedures described in General Method Four, morpholine (24 mmol) and K$_2$CO$_3$ (8 mmol) are added. The hydrochloride of N,N-dimethyl-3-(benzothiophen-2-yl)-3-morpholinyl-propylamine (VI-25) is obtained according to General Method Four as a white solid (1.38 g). The yield is 45.9%. Mp=220.8-223.9° C., MS(m/z): 305.3 [M+1]$^+$.

$^1$H NMR (DMSO-d$_6$)+D$_2$O: δ: 2.49-2.51 (m, 1H, —CH$_2$CH$_2$N—), 2.75 (s, 6H, N(CH$_3$)$_2$), 2.75-2.83 (m, 2H, —CH$_2$CH$_2$N—), 3.07 (m, 1H, —CH$_2$CH$_2$—), 3.07-3.28 (m, 4H, —NCH$_2$CH$_2$O), 3.85-3.92 (m, 4H, —NCH$_2$CH$_2$O), 4.95-4.98 (dd, J$_1$=2.4 Hz, J$_2$=11.2 Hz, 1H, Ar—CH—), 7.43-7.47 (m, 2H, Ar—H), 7.79 (s, 1H, Ar—H), 7.90-7.93 (m, 1H, Ar—H), 8.00-8.03 (m, 1H, Ar—H).

Example 26

Preparation of the hydrochloride of N-methyl-N-benzyl-3-(benzothiophen-2-yl)-3-morpholinyl-propylamine (VI-26)

N-methyl-N-benzyl-3-(benzothiophen-2-yl)-3-hydroxypropylamine hydrochloride (8 mmol), triethylamine (9.6 mmol) and p-methyl benzenesulfonyl chloride (8.8 mmol) are dissolved in acetonitrile (30 mL). Following procedures described in General Method Four, morpholine (24 mmol) and K$_2$CO$_3$ (8 mmol) are added. The hydrochloride of N-methyl-N-benzyl-3-(benzothiophen-2-yl)-3-morpholinyl-propylamine (VI-26) is obtained according to General Method Four as a white solid (1.56 g). The yield is 43.2%. Mp=312.2-314.0° C., MS(m/z): 381.2 [M+1]$^+$.

$^1$H NMR (DMSO-d$_6$): δ: 2.67 (s, 3H, —NCH$_3$), 2.78-2.93 (m, 2H, —CH$_2$CH$_2$N—), 2.98-3.16 (m, 4H, —NCH$_2$CH$_2$O), 3.79-3.81 (m, 2H, —CH$_2$CH$_2$N—), 3.91-4.02 (m, 4H, —NCH$_2$CH$_2$O), 4.23-4.31 (m, 2H, Ar—CH$_2$—), 5.03 (s, 1H, Ar—CH—), 7.32-7.35 (m, 3H, Ar—H), 7.40-7.46 (m, 2H, Ar—H), 7.56-7.58 (m, 2H, Ar—H), 7.75 (s, 1H, Ar—H), 7.87-7.90 (m, 1H, Ar—H), 7.99-8.02 (m, 1H, Ar—H), 9.56 (br, 1H, HCl, +D$_2$O vanished), 11.38 (br, 1H, HCl, +D$_2$O vanished).

Example 27

Preparation of the hydrochloride of N-methyl-3-(benzothiophen-2-yl)-3-morpholinyl-propylamine (VI-27)

A hydrogenation reaction at normal temperature and pressure is performed in the solution of N-methyl-N-benzyl-3-(benzothiophen-2-yl)-3-morpholinyl-propylamine hydrochloride (5 mmol) in methanol (30 mL) with 5% Pd/C (0.2 g) for 2 h. After the reaction, the Pd/C is removed through filtration and the filtrate is concentrated to give a white solid. Recrystalization of the white solid with anhydrous ethanol (10 mL) yields the hydrochloride of N-methyl-3-(benzothiophen-2-yl)-3-morpholinyl-propylamine (VI-27) (1.18 g). The yield is 65.3%. Mp=192.3-194.6° C., MS(m/z): 291.1 [M+1]$^+$.

$^1$H NMR (DMSO-d$_6$)+D$_2$O: δ: 2.51-2.53 (m, 2H, —CH$_2$CH$_2$N—), 2.97-3.03 (m, 2H, —CH$_2$CH$_2$N—), 3.07-3.28 (m, 4H, —NCH$_2$CH$_2$O), 3.45 (s, 3H, N—CH$_3$), 3.87-3.92 (m, 4H, —NCH$_2$CH$_2$O), 4.93-4.95 (d, J=9.6 Hz, 1H, Ar—CH—), 7.23 (s, 1H, Ar—H), 7.42-7.44 (m, 2H, Ar—H), 8.02-8.05 (t, J=8.4 Hz, 2H, Ar—H).

Example 28

Preparation of the hydrochloride of N,N-dimethyl-3-(benzothiophen-3-yl)-3-morpholinyl-propylamine (VI-28)

N,N-dimethyl-3-(benzothiophen-3-yl)-3-hydroxy-propylamine hydrochloride (8 mmol), triethylamine (9.6 mmol) and p-methyl benzenesulfonyl chloride (8.8 mmol) are dissolved in acetonitrile (30 mL). Following procedures described in General Method Four, morpholine (24 mmol) and K$_2$CO$_3$ (8 mmol) are added. The hydrochloride of N,N-dimethyl-3-(benzothiophen-3-yl)-3-morpholinyl-propylamine (VI-28) is obtained according to General Method Four as a white solid (1.41 g). The yield is 46.8%. Mp=228.9-231.6° C., MS(m/z): 305.3 [M+1]$^+$.

$^1$H NMR (CDCl$_3$-d): δ: 2.82-2.85 (m, 2H, —CH$_2$CH$_2$N—), 2.87-2.91 (m, 2H, —CH$_2$CH$_2$N—), 2.87-3.01 (m, 2H, —NCH$_2$CH$_2$O), 3.26-3.30 (br, 6H, N(CH$_3$)$_2$), 3.86-3.89 (m, 2H, —NCH$_2$CH$_2$O), 3.99-4.05 (m, 2H, —NCH$_2$CH$_2$O), 4.11-4.17 (m, 1H, —NCH$_2$CH$_2$O), 4.28-4.34 (m, 1H, —NCH$_2$CH$_2$O), 5.48-5.50 (d, J=6.4 Hz, 1H, Ar—CH—), 7.44-7.63 (m, 2H, Ar—H), 7.87-7.99 (m, 1H, Ar—H), 8.20 (s, 1H, Ar—H), 8.62 (s, 1H, Ar—H), 11.92 (br, 1H, HCl, +D$_2$O vanished), 12.61 (br, 1H, HCl, +D$_2$O vanished).

Example 29

Preparation of the hydrochloride of N-methyl-N-benzyl-3-(benzothiophen-3-yl)-3-morpholinyl-propylamine (VI-29)

N-methyl-N-benzyl-3-(benzothiophen-3-yl)-3-hydroxypropylamine hydrochloride (8 mmol), triethylamine (9.6 mmol) and p-methyl benzenesulfonyl chloride (8.8 mmol) are dissolved in acetonitrile (30 mL). Following procedures described in General Method Four, morpholine (24 mmol) and $K_2CO_3$ (8 mmol) are added. The hydrochloride of N-methyl-N-benzyl-3-(benzothiophen-3-yl)-3-morpholinyl-propylamine (VI-29) is obtained according to General Method Four as a white solid (1.85 g). The yield is 51.2%. Mp=320.5-323.0° C., MS(m/z): 381.2 $[M+1]^+$.

$^1$H NMR (DMSO-$d_6$): δ: 2.65 (s, 3H, —NCH$_3$), 2.75-2.56 (m, 2H, —CH$_2$CH$_2$N—), 2.97-3.13 (m, 4H, —NCH$_2$CH$_2$O), 3.75-3.80 (m, 2H, —CH$_2$CH$_2$N—), 3.92-4.03 (m, 4H, —NCH$_2$CH$_2$O), 4.25-4.31 (m, 2H, Ar—CH$_2$—), 5.05 (s, 1H, Ar—CH—), 7.30-7.33 (m, 3H, Ar—H), 7.38-7.44 (m, 2H, Ar—H), 7.49 (s, 1H, Ar—H), 7.59-7.64 (m, 2H, Ar—H), 7.99-8.02 (m, 2H, Ar—H), 9.56 (br, 1H, HCl, +D$_2$O vanished), 11.38 (br, 1H, HCl, +D$_2$O vanished).

Example 30

Preparation of the hydrochloride of N-methyl-3-(benzothiophen-3-yl)-3-morpholinyl-propylamine (VI30)

A hydrogenation reaction at normal temperature and pressure is performed in the solution of N-methyl-N-benzyl-3-(benzothiophen-3-yl)-3-morpholinyl-propylamine hydrochloride (5 mmol) in methanol (30 mL) with 5% Pd/C (0.2 g) for 2 h. After the reaction, the Pd/C is removed through filtration and the filtrate is concentrated to give a white solid. Recrystalization of the white solid with anhydrous ethanol (10 mL) yields the hydrochloride of N-methyl-3-(benzothiophen-3-yl)-3-morpholinyl-propylamine (VI-30) (1.36 g). The yield is 75.0%. Mp=197.5-198.6° C., MS(m/z): 291.1 $[M+1]^+$.

$^1$H NMR (DMSO-$d_6$)+D$_2$O: δ: 2.49-2.51 (m, 2H, —CH$_2$CH$_2$N—), 2.96-3.00 (m, 2H, —CH$_2$CH$_2$N—), 3.05-3.25 (m, 4H, —NCH$_2$CH$_2$O), 3.47 (s, 3H, N—CH$_3$), 3.85-3.90 (m, 4H, —NCH$_2$CH$_2$O), 4.91-4.94 (d, J=9.6 Hz, 1H, Ar—CH—), 7.40-7.43 (m, 2H, Ar—H), 7.49 (s, 1H, Ar—H), 8.03-8.05 (t, J=8.4 Hz, 2H, Ar—H).

Example 31

Preparation of the hydrochloride of N,N-dimethyl-3-(indol-3-yl)-3-morpholinyl-propylamine (VI-31)

3-acetylindole (20 mmol), dimethylamine hydrochloride (22 mmol) and polyformaldehyde (26 mmol) are dissolved in 95% ethanol (10 mL) and added with concentrated HCl (0.05 mL). Following procedures described in General Method Two-Method C, a white solid is obtained (4.31 g). The yield is 85.5%. MS(m/z): 217.2 $[M+1]^+$.

The product obtained above (10 mmol) and NaBH$_4$ (10 mmol) are dissolved in methanol (50 mL). Following procedures described in General Method. Three, a white solid is obtained (2.37 g). The yield is 93.2%. MS(m/z): 219.1 $[M+1]^+$.

The product from the previous step (8 mmol), triethylamine (9 6 mmol) and p-methyl benzenesulfonyl chloride (8.8 mmol) are dissolved in acetonitrile (30 mL). Following procedures described in General Method. Four, morpholine (24 mmol) and $K_2CO_3$ (8 mmol) are added. The hydrochloride of N,N-dimethyl-3-(indol-3-yl)-3-morpholinyl-propylamine (VI-31) is obtained according to General Method Four as a white solid (1.24 g). The yield is 43.2%. Mp=232.5-234.8, MS(m/z): 288.3 $[M+1]^+$.

$^1$H NMR (CDCl$_3$-d): δ: 2.75-2.81 (m, 2H, —CH$_2$CH$_2$N—), 2.85-2.89 (m, 2H, —CH$_2$CH$_2$N—), 2.92-3.01 (m, 2H, —NCH$_2$CH$_2$O), 3.28-3.31 (br, 6H, N(CH$_3$)$_2$), 3.82-3.89 (m, 2H, —NCH$_2$CH$_2$O), 3.99-4.06 (m, 2H, —NCH$_2$CH$_2$O), 4.12-4.18 (m, 2H, —NCH$_2$CH$_2$O), 5.47-5.50 (d, J=6.4 Hz, 1H, Ar—CH—), 7.37-7.58 (m, 2H, Ar—H), 7.81-7.92 (m, 1H, Ar—H), 8.13 (s, 1H, Ar—H), 8.58 (s, 1H, Ar—H), 11.15 (s, 1H, NH).

Example 32

Preparation of the hydrochloride of N-methyl-N-benzyl-3-(indol-3-yl)-3-morpholinyl-propylamine (VI-32)

3-acetylindole (10 mmol), N-methylbenzylamine hydrochloride (11 mmol) and polyformaldehyde (13 mmol) are dissolved in 95% ethanol (10 mL) and added with concentrated HCl (0.03 mL). Following procedures described in General Method Two-Method C, a white solid is obtained (2.62 g). The yield is 79.8%. MS(m/z): 293.2 $[M+1]^+$.

The product obtained above (7 mmol) and NaBH$_4$ (7 mmol) are dissolved in methanol (30 mL). Following procedures described in General Method Three, a white solid is obtained (2.18 g). The yield is 94.5%. MS(m/z): 295.1 $[M+1]^+$.

The product from the previous step (6 mmol), triethylamine (7.2 mmol) and p-methyl benzenesulfonyl chloride (6.6 mmol) are dissolved in acetonitrile (30 mL). Following procedures described in General Method Four, morpholine (18 mmol) and $K_2CO_3$ (6 mmol) are added. The hydrochloride of N-methyl-N-benzyl-3-(indol-3-yl)-3-morpholinyl-propylamine (VI-32) is obtained according to General Method Four as a white solid (1.04 g). The yield is 40.0%. Mp=295.0-297.8° C., MS(m/z): 364.3 $[M+1]^+$.

$^1$H NMR (CDCl$_3$-d): δ: 2.45-2.51 (m, 2H, —CH$_2$CH$_2$N—), 2.69 (s, 3H, N—CH$_3$), 2.86-2.90 (m, 2H, —CH$_2$CH$_2$N—), 2.92-3.03 (m, 2H, —NCH$_2$CH$_2$O), 3.42-3.53 (m, 2H, —NCH$_2$CH$_2$O), 3.68-3.75 (m, 2H, —NCH$_2$CH$_2$O), 3.89-3.96 (m, 2H, —NCH$_2$CH$_2$O), 4.25-4.31 (m, 2H, Ar—CH$_2$—), 5.45-5.47 (d, J=6.4 Hz, 1H, Ar—CH—), 7.15-7.19 (m, 3H, Ar—H), 7.29-7.33 (m, 2H, Ar—H), 7.37-7.58 (m, 2H, Ar—H), 7.81-7.92 (m, 1H, Ar—H), 8.11 (s, 1H, Ar—H), 8.56 (s, 1H, Ar—H), 11.13 (s, 1H, NH).

Example 33

Preparation of the hydrochloride of N-methyl-3-(indol-3-yl)-3-morpholinyl-propylamine (VI33)

A hydrogenation reaction at normal temperature and pressure is performed in the solution of N-methyl-N-benzyl-3-(indol-3-yl)-3-morpholinyl-propylamine hydrochloride (3 mmol) in methanol (20 mL) with 5% Pd/C (0.1 g) for 2 h. After the reaction, the Pd/C is removed through filtration and the filtrate is concentrated to give a white solid. Recrystalization of the white solid with anhydrous ethanol (10 mL) yields the hydrochloride of N-methyl-3-(indol-3-yl)-3-morpholinyl-propylamine (VI-33) (0.81 g). The yield is 78.2%. Mp=178.0-178.6° C., MS(m/z): 274.3 [M+1]$^+$.

$^1$H NMR (DMSO-d$_6$)+D$_2$O: δ: 2.45-2.49 (m, 2H, —CH$_2$CH$_2$N—), 2.97-3.02 (m, 2H, —CH$_2$CH$_2$N—), 3.09-3.25 (m, 4H, —NCH$_2$CH$_2$O), 3.52 (s, 3H, N—CH$_3$), 3.87-3.93 (m, 4H, —NCH$_2$CH$_2$O), 4.90-4.93 (d, J=9.6 Hz, 1H, Ar—CH—), 7.42-7.58 (m, 2H, Ar—H), 7.81-7.90 (m, 1H, Ar—H), 8.10 (s, 1H, Ar—H), 8.59 (s, 1H, Ar—H), 11.13 (s, 1H, NH).

Example 34

Preparation of the hydrochloride of N,N-dimethyl-3-(5-chloro-6-methoxynaphthalen-2-yl)-3-morpholinyl-propylamine (VI34)

To the solution of 1-chloro-2-methoxynaphthalene (0.05 mol) dissolved in dichloromethane (30 mL), AlCl$_3$ (0.10 mol) is added batch by batch and 3-chloropropionyl chloride (0.055 mol) is added dropwise, while the internal temperature is maintained below 5° C. Following procedures described in General Method One-Method A, 3-chloro-1-(5-chloro-6-methoxynaphthalen-2-yl)-acetone is obtained as a white solid (12.7 g). The yield is 90.0%. MS(m/z): 283.0 [M+1]$^+$.

This intermediate (0.03 mol) and dimethylamine aqueous solution (0.15 mol) are dissolved in anhydrous ethanol (50 mL). Following procedures described in General Method Two-Method A, a white solid product is obtained (8.36 g). The yield is 85.2%. MS(m/z): 292.1 [M+1]$^+$.

The product obtained above (10 mmol) and NaBH$_4$ (10 mmol) are dissolved in methanol (50 mL). Following procedures described in General Method Three, a white solid is obtained (2.94 g). The yield is 89.5%. MS (m/z): 294.2 [M+1]$^+$.

The product from the previous step (8 mmol), triethylamine (9.6 mmol) and p-methyl benzenesulfonyl chloride (8.8 mmol) are dissolved in acetonitrile (30 mL). Following procedures described in General Method Four, morpholine (24 mmol) and K$_2$CO$_3$ (8 mmol) are added. The hydrochloride of N,N-dimethyl-3-(5-chloro-6-methoxynaphthalen-2-yl)-3-morpholinyl-propylamine (VI-34) is obtained according to General Method Four as a white solid (1.70 g). The yield is 48.9%. Mp=202.5-204.9° C., MS(m/z): 363.2 [M+1]$^+$.

$^1$H NMR (DMSO-d$_6$)+D$_2$O: δ: 2.42-2.61 (m, 2H, —CH$_2$CH$_2$N—), 2.68 (s, 6H, N(CH$_3$)$_2$), 2.75-2.83 (m, 2H, —CH$_2$CH$_2$N—), 2.90-2.95 (m, 4H, —NCH$_2$CH$_2$O), 3.72-3.78 (m, 4H, —NCH$_2$CH$_2$O), 4.00 (s, 3H, —OCH$_3$), 4.60-4.62 (d, J=8.8 Hz, 1H, Ar—CH—), 7.58-7.60 (d, J=8.8 Hz, 1H, Ar—H), 7.73-7.75 (dd, J$_1$=1.2 Hz, J$_2$=8.8 Hz, 1H, Ar—H), 7.96-7.99 (d, J=8.8 Hz, 1H, Ar—H), 8.05-8.08 (t, J=8.8 Hz, 2H, Ar—H).

Example 35

Preparation of the hydrochloride of N-methyl-N-benzyl-3-(5-chloro-6-methoxynaphthalen-2-yl)-3-morpholinyl-propylamine (VI35)

3-chloro-1-(5-chloro-6-methoxynaphthalen-2-yl)-acetone (0.05 mol), N-methylbenzylamine hydrochloride (0.05 mol) and diisopropyl ethylamine (0.15 mol) are dissolved in acetonitrile (100 mL). Following procedures described in General Method Two-Method B, a white solid product is obtained (17.6 g). The yield is 80.0%. MS(m/z): 368.2 [M+1]$^+$.

The intermediate obtained above (10 mmol) and NaBH$_4$ (10 mmol) are dissolved in methanol (50 mL). Following procedures described in General Method Three, a white solid is obtained (3.77 g). The yield is 85.4%. MS(m/z): 370.2 [M+1]$^+$.

The product from the previous step (8 mmol), triethylamine (9.6 mmol) and p-methyl benzenesulfonyl chloride (8.8 mmol) are dissolved in acetonitrile (30 mL). Following procedures described in General Method Four, morpholine (24 mmol) and K$_2$CO$_3$ (8 mmol) are added. The hydrochloride of N-methyl-N-benzyl-3-(5-chloro-6-methoxynaphthalen-2-yl)-3-morpholinyl-propylamine (VI-35) is obtained according to General Method Four as a white solid (1.81 g). The yield is 44.3%. Mp=248.1-250.3° C., MS(m/z): 439.4 [M+1]$^+$.

$^1$H NMR (DMSO-d$_6$)+D$_2$O: δ: 2.46-2.74 (m, 2H, —CH$_2$CH$_2$N—), 2.68 (s, 3H, —NCH$_3$), 2.84-2.94 (m, 2H, —CH$_2$CH$_2$N—), 2.96-3.01 (m, 4H, —NCH$_2$CH$_2$O), 3.86 (m, 4H, —NCH$_2$CH$_2$O), 4.01 (s, 3H, —OCH$_3$), 4.26 (s, 2H, Ar—CH$_2$—), 4.59-4.61 (d, J=8.8 Hz, 1H, Ar—CH—), 7.26-7.28 (t, J=6.4 Hz, 3H, Ar—H), 7.39-7.40 (d, J=6.0 Hz, 2H, Ar—H), 7.62-7.64 (d, J=9.2 Hz, 1H, Ar—H), 7.76-7.79 (dd, J$_1$=0.8 Hz, J$_2$=8.0 Hz, 1H, Ar—H), 7.96-7.99 (d, J=8.8 Hz, 1H, Ar—H), 8.09-8.11 (t, J=8.8 Hz, 2H, Ar—H).

Example 36

Preparation of the hydrochloride of N,N-dimethyl-3-(5-chloro-6-methoxynaphthalen-2-yl)-3-(pyrrolidin-1-yl)-propylamine (VI36)

N,N-dimethyl-3-(5-chloro-6-methoxynaphthalen-2-yl)-3-hydroxy-propylamine hydrochloride (8 mmol), triethylamine (9.6 mmol) and p-methyl benzenesulfonyl chloride (8.8 mmol) are dissolved in acetonitrile (30 mL). Following procedures described in General Method Four, tetrahydropyrrole (24 mmol) and K$_2$CO$_3$ (8 mmol) are added. The hydrochloride of N,N-dimethyl-3-(5-chloro-6-methoxynaphthalen-2-yl)-3-(pyrrolidin-1-yl)-propylamine (VI-36) is obtained according to General Method Four as a white solid (1.5 g). The yield is 44.9%. Mp=215.2-216.9° C., MS (m/z):347.2 [M+1]$^+$.

$^1$H NMR (DMSO-d6): δ: 1.93 (m, 4H, —NCH$_2$CH$_2$CH$_2$CH$_2$N—), 2.51-2.62 (m, 2H, NCHCH$_2$CH$_2$N), 2.63-2.74 (m, 2H, —NCH$_2$CH$_2$CH$_2$CH$_2$N—), 2.68 (s, 6H, —NCH$_3$), 2.91-2.97 (m, 2H, —NCH$_2$CH$_2$CH$_2$N—), 3.07 (m, 2H, NCHCH$_2$CH$_2$N), 4.02 (s, 3H, —OCH$_3$), 4.66-4.70 (dd, J$_1$=4.0 Hz, J$_2$=9.6 Hz, 1H, NCHCH$_2$CH$_2$N), 5.28-5.36 (m, 1H, NCH$_2$CH=), 7.64-7.66 (d, J=9.2 Hz, 1H, Ar—H), 7.98-8.00 (d, J=8.8 Hz, 1H, Ar—H), 8.05-8.07 (d, J=8.8 Hz, 1H, Ar—H), 8.17-8.19 (d, J=8.8 Hz, 1H, Ar—H), 8.25 (s, 1H, Ar—H), 11.50 (br, 1H, HCl, +D$_2$O vanished).

Example 37

Preparation of the hydrochloride of N,N-dimethyl-3-(4-methoxyphenyl)-3-(pyrrolidin-1-yl)-propylamine (VI-37)

4-methoxyacetophenone (20 mmol), dimethylamine hydrochloride (22 mmol) and polyformaldehyde (26 mmol) are dissolved in 95% ethanol (10 mL) and added with concentrated HCl (0.05 mL). Following procedures described in General Method Two-Method C, a white solid is obtained (3.89 g). The yield is 80.0%. MS(m/z): 208.2 [M+1]$^+$.

The intermediate obtained above (10 mmol) and NaBH$_4$ (10 mmol) are dissolved in methanol (50 mL). Following procedures described in General Method Three, a white solid is obtained (2.28 g). The yield is 92.9%. MS(m/z): 210.1 [M+1]$^+$.

The product from the previous step (8 mmol), triethylamine (9.6 mmol) and p-methyl benzenesulfonyl chloride (8.8 mmol) are dissolved in acetonitrile (30 mL). Following procedures described in General Method Four, tetrahydropyrrole (24 mmol) and K$_2$CO$_3$ (8 mmol) are added. The hydrochloride of N,N-dimethyl-3-(4-methoxyphenyl)-3-(pyrrolidin-1-yl)-propylamine (VI-37) is obtained according to General Method Four as a white solid (1.07 g). The yield is 40.2%. Mp=175.2-178.4° C., MS(m/z): 263.4 [M+1]$^+$.

$^1$H NMR (DMSO-d$_6$)+D$_2$O: δ: 1.82-1.86 (m, 4H, —NCH$_2$CH$_2$CH$_2$CH$_2$N—), 2.53-2.58 (m, 2H, —CH$_2$CH$_2$N—), 2.68 (s, 6H, N(CH$_3$)$_2$), 2.90-2.97 (m, 2H, —CH$_2$CH$_2$N—), 3.13 (m, 4H, —NCH$_2$CH$_2$CH$_2$CH$_2$N—), 4.69 (s, 3H, —OCH$_3$), 4.94-4.97 (d, J=9.6 Hz, 1H, Ar—CH—), 6.62-6.65 (d, J=8.8 Hz, 2H, Ar—H), 7.26-7.29 (t, J=8.8 Hz, 2H, Ar—H).

Example 38

Preparation of the hydrochloride of N,N-dimethyl-3-(4-methoxyphenyl)-3-morpholinyl-propylamine (VI-38)

N,N-dimethyl-3-(4-methoxyphenyl)-3-hydroxy-propylamine hydrochloride (8 mmol), triethylamine (9.6 mmol) and p-methyl benzenesulfonyl chloride (8.8 mmol) are dissolved in acetonitrile (30 mL). Following procedures described in General Method Four, morpholine (24 mmol) and K$_2$CO$_3$ (8 mmol) are added. The hydrochloride of N,N-dimethyl-3-(4-methoxyphenyl)-3-morpholinyl-propylamine (VI-38) is obtained according to General Method Four as a white solid (1.12 g). The yield is 40.0%. Mp=184.0-187.2° C., MS(m/z): 279.4 [M+1]$^+$.

$^1$H NMR (CDCl$_3$+DMSO-d$_6$): δ: 2.14-2.41 (m, 2H, —CH$_2$CH$_2$N—), 2.36-2.41 (ds, 6H, N(CH$_3$)$_2$), 2.47-2.74 (m, 4H, —NCH$_2$CH$_2$O), 3.29-3.87 (m, 4H, —NCH$_2$CH$_2$O), 3.41 (s, 3H, —OCH$_3$), 3.52-3.53 (d, J=4.8 Hz, 2H, —CH$_2$CH$_2$N—), 4.29-4.31 (d, J=8.4 Hz, 1H, Ar—CH—), 6.55-6.58 (d, J=8.4 Hz, 2H, Ar—H), 7.25-7.28 (t, J=8.4 Hz, 2H, Ar—H), 11.25 (br, 1H, HCl, +D$_2$O vanished), 12.00 (br, 1H, HCl, +D$_2$O vanished).

Example 39

Preparation of the hydrochloride of N,N,2-trimethyl-3-(4-methoxyphenyl)-3-morpholinyl-propylamine (VI-39)

4-methoxypropiophenone (20 mmol), dimethylamine hydrochloride (22 mmol) and polyformaldehyde (26 mmol) are dissolved in 95% ethanol (10 mL) and added with concentrated HCl (0.05 mL). Following procedures described in General Method Two-Method C, a white solid is obtained (3.95 g). The yield is 76.8%. MS(m/z): 222.1 [M+1]$^+$.

The product obtained above (10 mmol) and NaBH$_4$ (10 mmol) are dissolved in methanol (50 mL). Following procedures described in General Method Three, a white solid is obtained (2.35 g). The yield is 90.7%. MS(m/z): 224.1 [M+1]$^+$.

The product from the previous step (8 mmol), triethylamine (9.6 mmol) and p-methyl benzenesulfonyl chloride (8.8 mmol) are dissolved in acetonitrile (30 mL). Following procedures described in General Method Four, morpholine (24 mmol) and K$_2$CO$_3$ (8 mmol) are added. The hydrochloride of N,N,2-trimethyl-3-(4-methoxyphenyl)-3-morpholinyl-propylamine (VI-39) is obtained according to General Method Four as a white solid (1.44 g). The yield is 49.5%. Mp=235.6-238.9° C., MS(m/z): 293.4 [M+1]$^+$.

$^1$H NMR (DMSO-d$_6$)+D$_2$O: δ: 0.98 (d, J=7.6 Hz, 3H, CHCH$_3$), 2.20-2.25 (m, 2H, —ArCHCHCH$_2$N—), 2.65 (s, 6H, N(CH$_3$)$_2$), 2.70-2.75 (m, 1H, —ArCHCHCH$_2$N—), 2.97-3.05 (m, 4H, —NCH$_2$CH$_2$O), 3.24-3.29 (m, 4H, —NCH$_2$CH$_2$O), 4.69 (s, 3H, —OCH$_3$), 4.21-4.23 (d, J=8.8 Hz, 1H, Ar—CH—), 6.56-6.58 (d, J=8.4 Hz, 2H, Ar—H), 7.26-7.29 (t, J=8.4 Hz, 2H, Ar—H).

Example 40

Preparation of the hydrochloride of N,N-dimethyl-2-((3,4-dichlorophenyl)(morpholine)methyl)-1-heptylamine (VI40)

AlCl$_3$ (0.07 mol) is added to 1,2-dichlorobenzene (0.07 mol). The mixture is heated to 70° C. and added with heptanoyl chloride (0.11 mol) dropwise while stirring. Following procedures described in General Method One-Method B, 1-(3,4-dichlorophenyl)-heptanone which is a white solid, is obtained (16.0 g). The yield based on 1,2-dichlorobenzene is 88.6%. MS(m/z): 259.1 [M+1]$^+$.

This intermediate (50 mmol), dimethylamine hydrochloride (55 mmol) and polyformaldehyde (65 mmol) are dissolved in 95% ethanol (10 mL) and added with concentrated HCl (0.2 mL). Following procedures described in General Method Two-Method C, a white solid is obtained (14.2 g). The yield is 80.9%. MS(m/z): 316.1 [M+1]$^+$.

The product obtained above (10 mmol) and NaBH$_4$ (10 mmol) are dissolved in methanol (50 mL). Following procedures described in General Method Three, a white solid is obtained (2.8 g). The yield is 79.3%. MS(m/Z): 318.1 [M+1]$^+$.

The product from the previous step (8 mmol), triethylamine (9.6 mmol) and p-methyl benzenesulfonyl chloride (8.8 mmol) are dissolved in acetonitrile (30 mL). Following procedures described in General Method Four, morpholine (24 mmol) and K$_2$CO$_3$ (8 mmol) are added. The hydrochloride of N,N-dimethyl-2-((3,4-dichlorophenyl)(morpholine)methyl)-1-heptylamine (VI-40) is obtained according to General Method Four as a white solid (1.8 g). The yield is 49.1%. MS(m/z): 387.2 [M+1]$^+$.

$^1$H NMR (DMSO-d$_6$): δ: 0.92 (t, J=7.2 Hz, 3H, CH$_2$CH$_3$), 1.35 (m, 3H, CH(CH$_2$)$_4$CH$_3$), 2.18-2.23 (m, 2H, —ArCHCHCH$_2$N—), 2.66 (s, 6H, N(CH$_3$)$_2$), 2.70-2.73 (m, 1H, —ArCHCHCH$_2$N—), 2.99-3.03 (m, 4H, —NCH$_2$CH$_2$O), 3.21-3.26 (m, 4H, —NCH$_2$CH$_2$O), 4.65 (s, 1H, Ar—CH—), 7.75-7.77 (dd, J$_1$=8.4 Hz, J$_2$=3.2 Hz, 2H, Ar—H), 8.10 (s, 1H, Ar—H).

Example 41

Preparation of the hydrochloride of N,N-dimethyl-3-(2,3-dihydrobenzofuran-5-yl)-3-morpholinyl-propylamine (VI-41)

To the solution of 2,3-dihydrobenzofuran (0.05 mol) dissolved in dichloromethane (30 mL), AlCl$_3$ (0.10 mol) is added batch by batch and 3-chloropropionyl chloride (0.055 mol) is added dropwise, while the internal temperature is maintained below 5° C. Following procedures described in General Method One-Method A, 3-chloro-1-(2,3-dihydrobenzofuran-5-yl)-acetone is obtained as a white solid (8.4 g). The yield is 80.2%. MS(m/z): 211.0 [M+1]$^+$.

This intermediate (0.03 mol) and dimethylamine aqueous solution (0.15 mol) are dissolved in anhydrous ethanol (50 mL). Following procedures described in General Method Two-Method A, a white solid product is obtained (5.78 g). The yield is 75.6%. MS(m/z): 220.2 [M+1]$^+$.

The product obtained above (10 mmol) and NaBH$_4$ (10 mmol) are dissolved in methanol (50 mL). Following procedures described in General Method Three, a white solid is obtained (2.38 g). The yield is 92.3%. MS(m/z): 222.2 [M+1]$^+$.

The product from the previous step (8 mmol), triethylamine (9.6 mmol) and p-methyl benzenesulfonyl chloride (8.8 mmol) are dissolved in acetonitrile (30 mL). Following procedures described in General Method Four, morpholine (24 mmol) and K$_2$CO$_3$ (8 mmol) are added. The hydrochloride of N,N-dimethyl-3-(2,3-dihydrobenzofuran-5-yl)-3-morpholinyl-propylamine (VI-41) is obtained according to General Method Four as a white solid (1.17 g). The yield is 40.5%. Mp=234.5-236.9° C., MS(m/z): 291.3 [M+1]$^+$.

$^1$H NMR (DMSO-d$_6$): δ: 1.99-2.22 (m, 2H, —CH$_2$CH$_2$N—), 2.36-2.48 (m, 2H, —CH$_2$CH$_2$N—), 2.69 (s, 6H, N(CH$_3$)$_2$), 2.75-2.89 (m, 4H, —NCH$_2$CH$_2$O), 3.01-3.04 (d, 2H, ArCH$_2$CH$_2$O), 3.63-3.68 (m, 4H, —NCH$_2$CH$_2$O), 3.76-3.78 (t, J=7.2 Hz, 1H, Ar—CH—), 4.25-4.28 (d, J=8.8 Hz, 2H, ArCH$_2$CH$_2$O), 7.21-7.23 (dd, J$_1$=1.6 Hz, J$_2$=8.0 Hz, 1H, Ar—H), 7.35-7.38 (dd, J$_1$=1.6 Hz, J$_2$=8.0 Hz, 1H, Ar—H), 7.62-7.64 (d, J=8.4 Hz, 1H, Ar—H), 10.51 (br, 1H, HCl, +D$_2$O vanished).

Example 42

Preparation of the hydrochloride of N-methyl-N-benzyl-3-(2,3-dihydrobenzofuran-5-yl)-3-morpholinyl-propylamine (VI-42)

3-chloro-1-(2,3-dihydrobenzofuran-5-yl)-acetone (0.02 mol), N-methylbenzylamine hydrochloride (0.02 mol) and diisopropyl ethylamine (0.06 mol) are dissolved in acetonitrile (60 mL). Following procedures described in General Method Two-Method B, a white solid product is obtained (5.20 g). The yield is 78.5%. MS(m/z): 296.2 [M+1]$^+$.

The intermediate obtained above (10 mmol) and NaBH$_4$ (10 mmol) are dissolved in methanol (50 mL). Following procedures described in General Method Three, a white solid is obtained (3.0 g). The yield is 90.2%. MS(m/z):

The product from the previous step (8 mmol), triethylamine (9.6 mmol) and p-methyl benzenesulfonyl chloride (8.8 mmol) are dissolved in acetonitrile (30 mL). Following procedures described in General Method Four, morpholine (24 mmol) and K$_2$CO$_3$ (8 mmol) are added. The hydrochloride of N-methyl-N-benzyl-3-(2,3-dihydrobenzofuran-5-yl)-3-morpholinyl-propylamine (VI-42) is obtained according to General Method Four as a white solid (1.4 g). The yield is 40.0%. Mp=265.0-268.5° C., MS(m/z): 367.4 [M+1]$^+$.

$^1$H NMR (DMSO-d$_6$)+D$_2$O: δ: 2.43-2.55 (m, 2H, —CH$_2$CH$_2$N—), 2.49-2.58 (m, 2H, —NCH$_2$CH$_2$O), 2.69 (s, 3H, —NCH$_3$), 2.83-2.91 (m, 2H, —CH$_2$CH$_2$N—), 3.01-3.08 (m, 2H, —NCH$_2$CH$_2$O), 3.12-3.15 (d, J=8.8 Hz, 2H, ArCH$_2$CH$_2$O), 3.62-3.69 (m, 4H, —NCH$_2$CH$_2$O), 4.21 (s, 2H, Ar—CH$_2$—), 4.29-4.31 (d, J=6.4 Hz, 1H, Ar—CH—), 4.27-4.30 (d, J=8.8 Hz, 2H, ArCH$_2$CH$_2$O), 7.30-7.36 (m, 6H, Ar—H), 7.62-7.64 (d, J=8.4 Hz, 1H, Ar—H), 7.72 (d, J=2.0 Hz, 1H, Ar—H).

Example 43

Preparation of the hydrochloride of N-methyl-3-(2,3-dihydrobenzofuran-5-yl)-3-morpholinyl-propylamine (VI-43)

A hydrogenation reaction at normal temperature and pressure is performed in the solution of N-methyl-N-benzyl-3-(2,3-dihydrobenzofuran-5-yl)-3-morpholinyl-propylamine hydrochloride (3 mmol) in methanol (20 mL) with 5% Pd/C (0.1 g) for 2 h. After the reaction, the Pd/C is removed through filtration and the filtrate is concentrated to give a white solid. Recrystalization of the white solid with anhydrous ethanol (10 mL) yields the hydrochloride of N-methyl-3-(2,3-dihydrobenzo furan-5-yl)-3-morpholinyl-propylamine (VI-43) (0.89 g). The yield is 85.0%. Mp=172.5-175.9° C., MS(m/z): 277.3 [M+1]$^+$.

$^1$H NMR (DMSO-d$_6$)+D$_2$O: δ: 2.35-2.42 (m, 2H, —CH$_2$CH$_2$N—), 2.71-2.79 (m, 2H, —CH$_2$CH$_2$N—), 3.02-3.07 (m, 4H, —NCH$_2$CH$_2$O), 3.10-3.13 (d, J=8.8 Hz, 2H, ArCH$_2$CH$_2$O), 3.25 (s, 3H, —NCH$_3$), 3.61-3.67 (m, 4H, —NCH$_2$CH$_2$O), 4.27-4.30 (d, J=8.0 Hz, 1H, Ar—CH—), 4.37-4.39 (d, J=8.8 Hz, 2H, ArCH$_2$CH$_2$O), 7.28-7.31 (d, J=8.4 Hz, 1H, Ar—H), 7.60-7.63 (d, J=8.4 Hz, 1H, Ar—H), 7.72 (s, 1H, Ar—H).

Example 44

Preparation of the hydrochloride of N,N-dimethyl-4-(3,4-dichlorophenyl)-4-morpholinyl-butylamine (VI-44)

AlCl$_3$ (0.1 mol) is added to 1,2-dichlorobenzene (0.1 mol). The mixture is heated to 70° C. and added with 4-chlorobutanoyl chloride (0.11 mol) dropwise. Following procedures described in General Method One-Method B, 4-chloro-1-(3,4-dichlorophenyl)-butanone which is a white solid, is obtained (21.0 g). The yield based on 1,2-dichlorobenzene is 84.0%. MS(m/z): 251.1 [M+1]$^+$.

This intermediate (0.05 mol) and dimethylamine aqueous solution (0.25 mol) are dissolved in anhydrous ethanol (100 mL). Following procedures described in General Method Two-Method. A, a white solid product is obtained (11.5 g). The yield is 81.9%. MS(m/z): 260.1 [M+1]$^+$.

The product obtained above (10 mmol) and NaBH$_4$ (10 mmol) are dissolved in methanol (50 mL). Following procedures described in General Method Three, a white solid is obtained (2.7 g). The yield is 90.9%. MS(m/z): 262.2 [M+1]$^+$.

The product from the previous step (8 mmol), triethylamine (9.6 mmol) and p-methyl benzenesulfonyl chloride (8.8 mmol) are dissolved in acetonitrile (30 mL). Following procedures described in General Method Four, morpholine (24 mmol) and K$_2$CO$_3$ (8 mmol) are added. The hydrochloride of N,N-dimethyl-4-(3,4-dichlorophenyl)-4-morpholinyl-butylamine (VI-44) is obtained according to General Method Four as a white solid (1.6 g). The yield is 49.8%. Mp=232.3-233.7° C., MS(m/z): 331.2 [M+1]$^+$.

$^1$H NMR (DMSO-d$_6$)+D$_2$O: δ:1.89-1.93 (m, 2H, —CHCH$_2$CH$_2$CH$_2$N—), 1.97-2.01 (m, 2H, —CHCH$_2$CH$_2$CH$_2$N—), 2.69 (s, 6H, N(CH$_3$)$_2$), 2.75-2.79 (m, 2H, CHCH$_2$CH$_2$CH$_2$N—), 2.94-3.00 (m, 4H, —NCH$_2$CH$_2$O), 3.75 (m, 4H, —NCH$_2$CH$_2$O), 4.66-4.68 (d, J=8.0 Hz, 1H, Ar—CH—), 7.26-7.28 (dd, J$_1$=2.0 Hz, J$_2$=8.4 Hz, 1H, Ar—H), 7.48 (d, J=2.0 Hz, 1H, Ar—H), 7.61-7.63 (d, J=8.0 Hz, 1H, Ar—H).

Example 45

Preparation of the hydrochloride of N,N-dimethyl-4-(3,4-dichlorophenyl)-4-(piperazin-1-yl)-butylamine (VI-45)

N,N-dimethyl-4-(3,4-dichlorophenyl)-4-hydroxy-butylamine hydrochloride (8 mmol), triethylamine (9.6 mmol) and p-methyl benzenesulfonyl chloride (8.8 mmol) are dissolved in acetonitrile (30 mL). Following procedures described in General Method Four, piperazine (24 mmol) and $K_2CO_3$ (8 mmol) are added. The hydrochloride of N,N-dimethyl-4-(3,4-dichlorophenyl)-4-(piperazin-1-yl)-butylamine (VI-45) is obtained according to General Method Four as a white solid (1.51 g). The yield is 43.2%. Mp=245.6-248.2° C., MS(m/z): 330.3 [M+1]$^+$.

$^1$H NMR (DMSO-d$_6$)+D$_2$O: δ:1.90-1.93 (m, 2H, —CHCH$_2$CH$_2$N—), 1.95-1.98 (m, 2H, —CHCH$_2$CH$_2$N—), 2.69 (s, 6H, N(CH$_3$)$_2$), 2.75-2.78 (m, 2H, CHCH$_2$CH$_2$N—), 2.92-2.96 (m, 4H, —NCH$_2$CH$_2$NH), 2.99-3.03 (m, 4H, —NCH$_2$CH$_2$NH), 4.65-4.67 (d, J=8.0 Hz, 1H, Ar—CH—), 7.25-7.27 (dd, J$_1$=2.0 Hz, J$_2$=8.4 Hz, 1H, Ar—H), 7.49 (d, J=2.01-1z, 1H, Ar—H), 7.58-7.60 (d, J=8.0 Hz, 1H, Ar—H).

Example 46

Preparation of the hydrochloride of N,N-dimethyl-4-(benzothiophen-3-yl)-4-morpholinyl-butylamine (VI-46)

To the solution of benzothiophene (0.05 mol) dissolved in dichloromethane (30 mL), AlCl$_3$ (0.10 mol) is added batch by batch and 4-chlorobutanoyl chloride (0.055 mol) is added dropwise, while the internal temperature is maintained below 5° C. Following procedures described in General Method One-Method. A, 4-chloro-1-(benzothiophen-3-yl)-butanone is obtained as a white solid (9.5 g). The yield is 79.8%. MS(m/z): 239.0 [M+1]$^+$.

This intermediate (0.03 mol) and dimethylamine aqueous solution (0.15 mol) are dissolved in anhydrous ethanol (50 mL). Following procedures described in General Method Two-Method A, a white solid product is obtained (6.7 g). The yield is 78.9%. MS(m/z): 248.1 [M+1]$^+$.

The product obtained above (10 mmol) and NaBH$_4$ (10 mmol) are dissolved in methanol (50 mL). Following procedures described in General Method Three, a white solid is obtained (2.43 g). The yield is 85.3%. MS(m/z): 250.1 [M+1]$^+$.

The product from the previous step (8 mmol), triethylamine (9.6 mmol) and p-methyl benzenesulfonyl chloride (8.8 mmol) are dissolved in acetonitrile (30 mL). Following procedures described in General Method Four, morpholine (24 mmol) and $K_2CO_3$ (8 mmol) are added. The hydrochloride of N,N-dimethyl-4-(benzothiophen-3-yl)-4-morpholinyl-butylamine (VI-46) is obtained according to General Method Four as a white solid (1.54 g). The yield is 49.4%. Mp=242.7-244.2° C., MS(m/z): 319.1 [M+1]$^+$.

$^1$H NMR (DMSO-d$_6$)+D$_2$O: δ: 1.87-1.90 (m, 2H, —CHCH$_2$CH$_2$N—), 1.95-1.98 (m, 2H, —CHCH$_2$CH$_2$N—), 2.67 (s, 6H, N(CH$_3$)$_2$), 2.73-2.76 (m, 2H, CHCH$_2$CH$_2$N—), 2.94-2.98 (m, 4H, —NCH$_2$CH$_2$O), 3.73 (m, 4H, —NCH$_2$CH$_2$O), 5.48-5.50 (d, J=6.4 Hz, 1H, Ar—CH—), 7.44-7.63 (m, 2H, Ar—H), 7.87-7.99 (m, 1H, Ar—H), 8.20 (s, 1H, Ar—H), 8.62 (s, 1H, Ar—H).

Example 47

Preparation of the hydrochloride of N,N-dimethyl-4-(benzothiophen-3-yl)-4-(piperazin-1-yl)-butylamine (VI-47)

N,N-dimethyl-4-(benzothiophen-3 -yl)-4-hydroxy-butylamine hydrochloride (8 mmol), triethylamine (9 6 mmol) and p-methyl benzenesulfonyl chloride (8.8 mmol) are dissolved in acetonitrile (30 mL). Following procedures described in General Method Four, piperazine (24 mmol) and $K_2CO_3$ (8 mmol) are added. The hydrochloride of N,N-dimethyl-4-(benzothiophen-3- yl)-4-(piperazin-1-yl)-butylamine (VI-47) is obtained according to General Method Four as a white solid (1.68 g). The yield is 49.4%. Mp249.6-252.2° C., MS(m/z): 318.1 [M+1]$^+$.

$^1$H NMR (DMSO-d$_6$)+D$_2$O: δ:1.90-1.92 (m, 2H, —CHCH$_2$CH$_2$N—), 1.96-1.99 (m, 2H, —CHCH$_2$CH$_2$N—), 2.65 (s, 6H, N(CH$_3$)$_2$), 2.72-2.75 (m, 2H, CHCH$_2$CH$_2$N—), 2.92-2.95 (m, 4H, —NCH$_2$CH$_2$NH), 2.97-3.01 (m, 4H, —NCH$_2$CH$_2$NH), 5.45-5.47 (d, J=6.4 Hz, 1H, Ar—CH—), 7.44-7.52 (m, 2H, Ar—H), 7.87-7.95 (m, 1H, Ar—H), 8.18 (s, 1H, Ar—H), 8.59 (s, 1H, Ar—H).

Example 48

Preparation of the hydrochloride of N,N-dimethyl-3-(2,4-difluorophenyl)-3-morpholinyl-propylamine (VI-48)

2,4-difluorobenzophenone (20 mmol), dirnethylamine hydrochloride (22 mmol) and polyformaldehyde (26 mmol) are dissolved in 95% ethanol (10 mL) and added with concentrated HCl (0.05 mL). Following procedures described in General Method Two-Method C, a white solid is obtained (4.23 g). The yield is 85.0%. MS(m/z): 214.0 [M+1]$^+$.

The intermediate obtained above (10 mmol) and NaBH$_4$ (10 mmol) are dissolved in methanol (50 mL). Following procedures described in General Method Three, a white solid is obtained (2.14 g). The yield is 85.2%. MS(m/z): 216.0 [M+1]$^+$.

The product from the previous step (8 mmol), triethylamine (9.6 mmol) and p-methyl benzenesulfonyl chloride (8.8 mmol) are dissolved in acetonitrile (30 mL). Following procedures described in General Method Four, morpholine (24 mmol) and $K_2CO_3$ (8 mmol) are added. The hydrochloride of N,N-dimethyl-3-(2,4-difluorophenyl)-3-morpholinyl-propylamine (VI-48) is obtained according to General Method Four as a white solid (1.57 g). The yield is 55.0%. Mp=245.8-248.0° C., MS(m/z): 285.2 [M+1]$^+$.

$^1$H NMR (DMSO-d$_6$): δ: 2.61-2.66 (m, 2H, —CH$_2$CH$_2$N—), 2.39-2.42 (m, 1H, —CH$_2$CH$_2$N—), 2.71 (s, 6H, N(CH$_3$)$_2$), 2.78-2.84 (m, 2H, —CH$_2$CH$_2$N—), 2.93-3.03 (m, 4H, —NCH$_2$CH$_2$O), 3.90 (m, 4H, —NCH$_2$CH$_2$O), 4.67-4.69 (d, J=7.2 Hz, 1H, Ar—CH—), 7.25-7.30 (m, 1H, Ar—H), 7.37-7.43 (m, 1H, Ar—H), 8.02-8.03 (d, 3-6.4 Hz, 1H, Ar—H), 10.95 (br, 1H, HCl, +D$_2$O vanished).

Example 49

Preparation of the hydrochloride of N-methyl-N-benzyl-3-(2,4-difluorobenyl)-3-morpholinyl-propylamine (VI-49)

2,4-difluorobenzophenone (20 mmol), N-methylaniline hydrochloride (22 mmol) and polyformaldehyde (26 mmol)

are dissolved in 95% ethanol (10 mL) and added with concentrated HCl (0.05 mL). Following procedures described in General Method Two-Method C, a white solid is obtained (4.55 g). The yield is 70.0%. MS(m/z): 290.1 [M+1]$^+$.

The intermediate obtained above (10 mmol) and NaBH$_4$ (10 mmol) are dissolved in methanol (50 mL). Following procedures described in General Method. Three, a white solid is obtained (2.95 g). The yield is 90.2%. MS (m/z): 292.0 [M+1]$^+$.

The product from the previous step (8 mmol), triethylamine (9 6 mmol) and p-methyl benzenesulfonyl chloride (8.8 mmol) are dissolved in acetonitrile (30 mL). Following procedures described in General Method Four, morpholine (24 mmol) and K$_2$CO$_3$ (8 mmol) are added. The hydrochloride of N-methyl-N-benzyl-3-(2,4-difluorophenyl)-3-morpholinyl-propylamine (VI-49) is obtained according to General Method Four as a white solid (2.07 g). The yield is 60.0%. Mp=228.5-231.2° C., MS(m/z): 361.2 [M+1]$^+$.

$^1$H NMR (DMSO-d$_6$)+D$_2$O: δ: 2.40-2.79 (m, 2H, —CH$_2$CH$_2$N—), 2.67 (s, 3H, —NCH$_3$), 2.86-3.05 (m, 2H, —CH$_2$CH$_2$N—), 3.47-3.67 (m, 4H, —NCH$_2$CH$_2$O), 3.74-3.75 (m, 4H, —NCH$_2$CH$_2$O), 4.27 (s, 2H, Ar—CH$_2$—), 4.45 (s, 1H, Ar—CH—), 7.12-7.17 (m, 1H, Ar—H), 7.23-7.28 (m, 1H, Ar—H), 7.37-7.41 (m, 3H, Ar—H), 7.42-7.50 (m, 2H, Ar—H), 7.65-7.71 (q, J=8.0 Hz, 1H, Ar—H).

Example 50

Preparation of the hydrochloride of N-methyl-3-(2,4-difluorophenyl)-3-morpholinyl-propylamine (VI-50)

A hydrogenation reaction at normal temperature and pressure is performed in the solution of N-methyl-N-benzyl-3-(2,4-difluorophenyl)-3-morpholinyl-propylamine hydrochloride (3 mmol) in methanol (20 mL) with 5% Pd/C (0.1 g) for 2 h. After the reaction, the Pd/C is removed through filtration and the filtrate is concentrated to give a white solid. Recrystalization of the white solid with anhydrous ethanol (10 mL) yields the hydrochloride of N-methyl-3-(2,4-difluorophenyl)-3-morpholinyl-propylamine (VI-50) (0.83 g). The yield is 80.9%. Mp=201.5-202.8° C., MS(m/z): 271.2 [M+1]$^+$.

$^1$H NMR (DMSO-d$_6$)+D$_2$O: δ: 2.40-2.68 (m, 2H, —CH$_2$CH$_2$N—), 2.65 (s, 3H, —NCH$_3$), 2.86-3.00 (m, 2H, —CH$_2$CH$_2$N—), 3.47-3.55 (m, 4H, —NCH$_2$CH$_2$O), 3.74-3.75 (m, 4H, —NCH$_2$CH$_2$O), 4.45 (s, 1H, Ar—CH—), 7.12-7.15 (m, 1H, Ar—H), 7.23-7.28 (m, 1H, Ar—H), 7.65-7.71 (q, J=8.0 Hz, 1H, Ar—H).

Example 51

Preparation of the hydrochloride of N,N-dimethyl-3-(3,4-dichlorophenyl)-3-(4-benzylpiperazinyl)-propylamine (VI51)

N,N-dimethyl-3-(3,4-dichlorophenyl)-3-hydroxy-propylamine hydrochloride (8 mmol), triethylamine (9.6 mmol) and p-methyl benzenesulfonyl chloride (8.8 mmol) are dissolved in acetonitrile (30 mL). Following procedures described in General Method Four, N-benzylpiperazine (24 mmol) and K$_2$CO$_3$ (8 mmol) are added. The hydrochloride of N,N-dimethyl-3-(3,4-dichlorophenyl)-3-(4-benzylpiperazinyl)-propylamine (VI-51) is obtained according to General Method Four as a white solid (1.72 g). The yield is 42.0%. Mp=238.5-241.9° C., MS(m/z):407.2 [M+1]$^+$.

$^1$H NMR (DMSO-d$_5$): δ: 2.31-2.62 (m, 2H, —CHCH$_2$CH$_2$N—), 2.71 (s, 6H, N(CH$_3$)$_2$), 2.79-2.81 (m, 2H, —CHCH$_2$CH$_2$N—), 2.97-3.01 (m, 2H, —NCH$_2$CH$_2$N—), 3.33 (s, 6H, —NCH$_2$CH$_2$N—), 4.33 (s, 2H, Ar—CH$_2$—), 4.42 (m, 1H, Ar—CH—), 7.41-7.46 (m, 3H, Ar—H), 7.49-7.51 (d, J=8.0 Hz, 1H, Ar—H), 7.60-7.62 (m, 2H, Ar—H), 7.69-7.71 (d, J=8.4 Hz, 1H, Ar—H), 7.80 (s, 1H, Ar—H), 10.82 (br, 1H, HCl, +D$_2$O vanished).

Example 52

Preparation of the hydrochloride of N,N-dimethyl-3-(3,4-dichlorophenyl)-3-(4-(3-(trifluoromethyl)phenyl)piperazinyl)-propylamine (VI-52)

N,N-dimethyl-3-(3,4-dichlorophenyl)-3-hydroxy-propylamine hydrochloride (8 mmol), triethylamine (9.6 mmol) and p-methyl benzenesulfonyl chloride (8.8 mmol) are dissolved in acetonitrile (30 mL). Following procedures described in General Method. Four, 4-(3-(trifluoromethyl)phenyl)piperazine (24 mmol) and K$_2$CO$_3$ (8 mmol) are added. The hydrochloride of N,N-dimethyl-3-(3,4-dichlorophenyl)-3-(4-(3-(trifluoromethyl)phenyl)piperazinyl)-propylamine (VI-52) is obtained according to General Method Four as a white solid (1.82 g). The yield is 40.2%. Mp=245.6-248.2° C., MS(m/z):460.1 [M+1]$^+$.

$^1$H NMR (DMSO-d$_6$)+D$_2$O: δ: 2.63-2.68 (m, 2H, —CHCH$_2$CH$_2$N—), 2.74 (s, 6H, N(CH$_3$)$_2$), 2.97-3.05 (m, 2H, —CHCH$_2$CH$_2$N—), 3.07-3.27 (m, 4H, —NCH$_2$CH$_2$N—), 3.50 (s, 4H, —NCH$_2$CH$_2$N—), 4.46-4.48 (d, J=8.8 Hz, 1H, Ar—CH—), 7.12-7.22 (m, 3H, Ar—H), 7.42-7.46 (t, J=8.0 Hz, 1H, Ar—H), 7.57-7.60 (q, J=1.6 Hz, 1H, Ar—H), 7.74-7.76 (d, J=8.0 Hz, 1H, Ar—H), 7.87-7.88 (d, J=1.6 Hz, 1H, Ar—H).

Example 53

Preparation of the hydrochloride of N-methyl-N-benzyl-3-(1,2-methylenedioxybenzen-4-yl)-3-piperidyl-propylamine (VI-53)

To the solution of 1,2-methylenedioxybenzene (0.05 mol) dissolved in dichloromethane (30 mL), AlCl$_3$ (0.10 mol) is added batch by batch and 3-chloropropionyl chloride (0.055 mol) is added dropwise, while the internal temperature is maintained below 5° C. Following procedures described in General Method One-Method A, 3-chloro-1-(1,2-methylenedioxybenzen-4-yl)-propanone is obtained as a white solid (9.5 g). The yield is 90.0%. MS(m/z): 213.0 [M+1]$^+$.

This intermediate (0.03 mol), N-methylbenzylamine hydrochloride (0.03 mol) and diisopropyl ethylamine (0.10 mol) are dissolved in acetonitrile (60 mL). Following procedures described in General Method Two-Method B, a white solid product is obtained (5.99 g). The yield is 60.0%. MS(m/z): 298.1 [M+1]$^+$.

The product obtained above (10 mmol) and NaBH$_4$ (10 mmol) are dissolved in methanol (50 mL) Following procedures described in General Method Three, a white solid is obtained (2.88 g). The yield is 85.9%. MS(m/z): 300.2 [M+1]$^+$.

The product from the previous step (8 mmol), triethylamine (9.6 mmol) and p-methyl benzenesulfonyl chloride (8.8 mmol) are dissolved in acetonitrile (30 mL). Following procedures described in General Method Four, piperidine (24 mmol) and K$_2$CO$_3$ (8 mmol) are added. The hydrochloride of N-methyl-N-benzyl-3-(1,2-methylenedioxybenzen-4-yl)-3-piperidyl-propylamine (VI-53) is obtained according to General Method Four as a white solid (1.49 g). The yield is 42.5%. Mp=285.6-288.9° C., MS(m/z): 367.4 [M+1]$^+$.

$^1$H NMR (DMSO-d$_6$) +D$_2$O: δ: 1.49-1.55 (m, 6H, —NCH$_2$CH$_2$CH$_2$CH$_2$CH$_2$N—), 2.35-2.41 (m, 2H, —CH$_2$CH$_2$N—), 2.68 (s, 3H, —NCH$_3$), 2.78-2.83 (m, 2H, —CH$_2$CH$_2$N—), 3.02-3.09 (m, 4H, —NCH$_2$CH$_2$CH$_2$CH$_2$CH$_2$N—), 4.19 (s, 2H, Ar—CH$_2$—), 4.27-4.29 (d, J=8.4 Hz, 1H, Ar—CH—), 6.12 (s, 2H, —OCH$_2$O—), 7.25-7.33 (m, 6H, Ar—H), 7.55-7.58 (d, J=8.4 Hz, 1H, Ar—H), 7.64-7.65 (d, J=2.0 Hz, 1H, Ar—H).

Example 54

Preparation of the hydrochloride of N-methyl-3-(1,2-methylenedioxybenzen-4-yl)-3-piperidyl-propylamine (VI-54)

A hydrogenation reaction at normal temperature and pressure is performed in the solution of N-methyl-N-benzyl-3-(1,2-methylenedioxybenzen-4-yl)-3-piperidyl-propylamine hydrochloride (3 mmol) in methanol (20 mL) with 5% Pd/C (0.1 g) for 2 h. After the reaction, the Pd/C is removed through filtration and the filtrate is concentrated to give a white solid. Recrystalization of the white solid with anhydrous ethanol (10 mL) yields the hydrochloride of N-methyl-3-(1,2-methylenedioxybenzen-4-yl)-3-piperidyl-propylamine (VI-54) (0.84 g). The yield is 80.5%. Mp=189.3-192.4° C., MS(m/z): 277.2 [M+1]$^+$.

$^1$H NMR (DMSO-d$_6$) +D$_2$O: δ: 1.53-1.58 (m, 6H, —NCH$_2$CH$_2$CH$_2$CH$_2$CH$_2$N—), 2.35-2.40 (m, 2H, —CH$_2$CH$_2$N—), 2.65-2.71 (m, 2H, —CH$_2$CH$_2$N—), 3.03-3.09 (m, 4H, —NCH$_2$CH$_2$CH$_2$CH$_2$CH$_2$N—), 3.26 (s, 3H, —NCH$_3$), 4.28-4.31 (d, J=8.0 Hz, 1H, Ar—CH—), 6.10 (s, 2H, —OCH$_2$O—), 7.23-7.25 (d, J=8.4 Hz, 1H, Ar—H), 7.58-7.61 (d, J=8.4 Hz, 1H, Ar—H), 7.72 (s, 1H, Ar—H).

Example 55

Preparation of the hydrochloride of N,N-dimethyl-3-(3,4-dimethoxyphenyl)-3-morpholinyl-propylamine (VI-55)

To the solution of 1,2-dimethoxybenzene (0.05 mol) dissolved in dichloromethane (30 mL), AlCl$_3$ (0.10 mol) is added batch by batch and 3-chloropropionyl chloride (0.055 mol) is added dropwise, while the internal temperature is maintained below 5° C. Following procedures described in General Method One-Method A, 3-chloro-1-(3,4-dimethoxyphenyl)-propanone is obtained as a white solid (10.3 g). The yield is 90.0%. MS(m/z): 229.0 [M+1]$^+$.

This intermediate (0.03 mol) and dimethylamine aqueous solution (0.15 mol) are dissolved in anhydrous ethanol (50 mL). Following procedures described in General Method Two-Method A, a white solid product is obtained (7.78 g). The yield is 95.0%. MS(m/z): 238.2 [M+1]$^+$.

The white solid obtained above (10 mmol) and NaBH$_4$ (10 mmol) are dissolved in methanol (50 mL). Following procedures described in General Method Three, a white solid is obtained (2.2 g). The yield is 80.0%. MS(m/z): 240.2 [M+1]$^+$.

The product from the previous step (8 mmol), triethylamine (9.6 mmol) and p-methyl benzenesulfonyl chloride (8.8 mmol) are dissolved in acetonitrile (30 mL). Following procedures described in General Method Four, morpholine (24 mmol) and K$_2$CO$_3$ (8 mmol) are added. The hydrochloride of N,N-dimethyl-3-(3,4-dimethoxyphenyl)-3-morpholinyl-propylamine (VI-55) is obtained according to General Method Four as a white solid (1.52 g). The yield is 50.0%. Mp=232.5-234.8° C., MS(m/z): 309.3 [M+1]$^+$.

$^1$H NMR (DMSO-d$_6$): δ: 1.87-1.98 (m, 2H, —CH$_2$CH$_2$N—), 2.32-2.45 (m, 2H, —CH$_2$CH$_2$N—), 2.70 (s, 6H, N(CH$_3$)$_2$), 2.73-2.80 (m, 4H, —NCH$_2$CH$_2$O), 3.60-3.64 (m, 4H, —NCH$_2$CH$_2$O), 3.71 (s, 6H, —OCH$_3$), 3.78-3.81 (t, J=8.0 Hz, 1H, Ar—CH—), 7.28-7.31 (dd, J$_1$=1.6 Hz, J$_2$=8.0 Hz, 1H, Ar—H), 7.36-7.38 (dd, J$_1$=1.6 Hz, J$_2$=8.0 Hz, 1H, Ar—H), 7.63 (s, 1H, Ar—H), 10.60 (br, 1H, HCl, +D$_2$O vanished).

Example 56

Preparation of the hydrochloride of N-methyl-N-benzyl-3-(3,4-dimethoxyphenyl)-3-morpholinyl-propylamine (VI-56)

3-chloro-1-(3,4-dimethoxyphenyl)-propanone (0.02 mol), N-methylbenzylamine hydrochloride (0.02 mol) and diisopropyl ethylamine (0.06 mol) are dissolved in acetonitrile (60 mL). Following procedures described in General Method Two-Method B, a white solid product is obtained (4.62 g). The yield is 60.0%. MS(m/z): 314.2 [M+1]$^+$.

The intermediate obtained above (10 mmol) and NaBH$_4$ (10 mmol) are dissolved in methanol (50 mL). Following procedures described in General Method Three, a white solid is obtained (3.29 g). The yield is 85.0%. MS(m/z): 316.1 [M+1]$^+$.

The product from the previous step (8 mmol), triethylamine (9.6 mmol) and p-methyl benzenesulfonyl chloride (8.8 mmol) are dissolved in acetonitrile (30 mL). Following procedures described in General Method Four, morpholine (24 mmol) and K$_2$CO$_3$ (8 mmol) are added. The hydrochloride of N-methyl-N-benzyl-3-(3,4-dimethoxyphenyl)-3-morpholinyl-propylamine (VI-56) is obtained according to General Method Four as a white solid (1.67 g). The yield is 45.8%. Mp=278.5-281.3° C., MS(m/z): 385.4 [M+1]$^+$.

$^1$H NMR (DMSO-d$_6$) +D$_2$O: δ: 2.25-2.34 (m, 2H, —CH$_2$CH$_2$N—), 2.41-2.52 (m, 2H, —NCH$_2$CH$_2$O), 2.68 (s, 3H, —NCH$_3$), 2.81-2.88 (m, 2H, —CH$_2$CH$_2$N—), 3.01-3.05 (m, 2H, —NCH$_2$CH$_2$O), 3.60-3.65 (m, 4H, —NCH$_2$CH$_2$O), 4.05 (s, 2H, Ar—CH$_2$—), 4.21 (s, 6H, —OCH$_3$), 4.29-4.31 (d, J=6.4 Hz, 1H, Ar—CH—), 7.12-7.14 (d, J=8.4 Hz, 1H, Ar—H), 7.19-7.22 (d, J=8.0 Hz, 1H, Ar—H) 7.34-7.38 (m, 6H, Ar—H).

Example 57

Preparation of the hydrochloride of N-methyl-3-(3,4-dimethoxyphenyl)-3-morpholinyl-propylamine (VI-57)

A hydrogenation reaction at normal temperature and pressure is performed in the solution of N-methyl-N-benzyl-3-(3,4-dimethoxyphenyl)-3-morpholinyl-propylamine hydrochloride (3 mmol) in methanol (20 mL) with 5% Pd/C (0.1 g) for 2 h. After the reaction, the Pd/C is removed through filtration and the filtrate is concentrated to give a white solid. Recrystalization of the white solid with anhydrous ethanol (10 mL) yields the hydrochloride of N-methyl-3-(3,4-dimethoxyphenyl)-3-morpholinyl-propylamine (VI-57) (0.84 g). The yield is 76.2%. Mp=200.2-203.4° C., MS(m/z): 295.2 [M+1]$^+$.

$^1$H NMR (DMSO-d$_6$) +D$_2$O: δ: 2.31-2.37 (m, 2H, —CH$_2$CH$_2$N—), 2.65-2.69 (m, 2H, —CH$_2$CH$_2$N—), 2.87-2.91 (m, 4H, —NCH$_2$CH$_2$O), 3.23 (s, 3H, —NCH$_3$), 3.61-3.65 (m, 4H, —NCH$_2$CH$_2$O), 4.19 (s, 6H, —OCH$_3$), 4.26-

4.28 (d, J=8.0 Hz, 1H, Ar—CH—), 7.27-7.29 (d, J=8.4 Hz, 1H, Ar—H), 7.58-7.61 (d, J=8.8 Hz, 1H, Ar—H), 7.71 (s, 1H, Ar—H).

Example 58

Preparation of the hydrochloride of N,N-dimethyl-3-(3,4-dimethoxyphenyl)-3-piperidyl-propylamine (VI-58)

N,N-dimethyl-3-(3,4-dimethoxyphenyl)-3-hydroxy-propylamine hydrochloride (8 mmol), triethylamine (9.6 mmol) and p-methyl benzenesulfonyl chloride (8.8 mmol) are dissolved in acetonitrile (30 mL). Following procedures described in General Method Four, piperidine (24 mmol) and $K_2CO_3$ (8 mmol) are added. The hydrochloride of N,N-dimethyl-3-(3,4-dimethoxyphenyl)-3-piperidyl-propylamine (VI-58) is obtained according to General Method Four as a white solid (1.27 g). The yield is 42.0%. Mp=220.3.5-224.0° C., MS(m/z): 307.2 [M+1]$^+$.

$^1$H NMR (DMSO-d$_6$) +D$_2$O: δ: 1.52-1.60 (m, 6H, —NCH$_2$CH$_2$CH$_2$CH$_2$N—), 2.02-2.10 (m, 2H, —CH$_2$CH$_2$N—), 2.29-2.36 (m, 2H, —CH$_2$CH$_2$N—), 2.70 (s, 6H, N(CH$_3$)$_2$), 3.10-3.15 (m, 4H, —NCH$_2$CH$_2$CH$_2$CH$_2$N—), 3.67 (s, 6H, —OCH$_3$), 3.75-3.78 (t, J=8.4 Hz, 1H, Ar—CH—), 7.21-7.23 (d, J=8.4 Hz, 1H, Ar—H), 7.50-7.53 (d, J=8.8 Hz, 1H, Ar—H), 7.69 (s, 1H, Ar—H).

Example 59

Preparation of the hydrochloride of N-methyl-N-benzyl-3-(3,4-dimethoxyphenyl)-3-piperidyl-propylamine (VI-59)

N-methyl-N-benzyl-3-(3,4-dimethoxyphenyl)-3-hydroxy-propylamine hydrochloride (8 mmol), triethylamine (9.6 mmol) and p-methyl benzenesulfonyl chloride (8.8 mmol) are dissolved in acetonitrile (30 mL). Following procedures described in General Method Four, piperidine (24 mmol) and $K_2CO_3$ (8 mmol) are added. The hydrochloride of N-methyl-N-benzyl-3-(3,4-dimethoxyphenyl)-3-piperidyl-propylamine (VI-59) is obtained according to General Method Four as a white solid (1.56 g). The yield is 43.0%. Mp=256.6-258.9° C., MS(m/z): 383.3 [M+1]$^+$.

$^1$H NMR (DMSO-d$_6$) +D$_2$O: δ: 1.48-1.53 (m, 6H, —NCH$_2$CH$_2$CH$_2$CH$_2$N—), 2.30-2.36 (m, 2H, —CH$_2$CH$_2$N—), 2.69 (s, 3H, —NCH$_3$), 2.80-2.85 (m, 2H, —CH$_2$CH$_2$N—), 3.11-3.16 (m, 4H, —NCH$_2$CH$_2$CH$_2$CH$_2$N—), 4.19 (s, 2H, Ar—CH$_2$—), 4.25 (s, 6H, —OCH$_3$), 4.29-4.31 (d, J=7.2 Hz, 1H, Ar—CH—), 7.13-7.16 (d, J=8.4 Hz, 1H, Ar—H), 7.22-7.25 (d, J=8.0 Hz, 1H, Ar—H), 7.35-7.39 (m, 6H, Ar—H).

Example 60

Preparation of the hydrochloride of N-methyl-3-(3,4-dimethoxyphenyl)-3-piperidyl-propylamine (VI-60)

A hydrogenation reaction at normal temperature and pressure is performed in the solution of N-methyl-N-benzyl-3-(3,4-dimethoxyphenyl)-3-piperidyl-propylamine hydrochloride (3 mmol) in methanol (20 mL) with 5% Pd/C (0.1 g) for 2 h. After the reaction, the Pd/C is removed through filtration and the filtrate is concentrated to give a white solid. Recrystalization of the white solid with anhydrous ethanol (10 mL) yields the hydrochloride of N-methyl-3-(3,4-dimethoxyphenyl)-3-piperidyl-propylamine (VI-60) (0.94 g). The yield is 85.7%. Mp=195.2-197.8° C., MS(m/z): 293.3 [M+1]$^+$.

$^1$H NMR (DMSO-d$_6$) +D$_2$O: δ: 1.45-1.50 (m, 6H, —NCH$_2$CH$_2$CH$_2$CH$_2$CH$_2$N—), 2.30-2.34 (m, 2H, —CH$_2$CH$_2$N—), 2.67-2.72 (m, 2H, —CH$_2$CH$_2$N—), 3.00-3.07 (m, 4H, —NCH$_2$CH$_2$CH$_2$CH$_2$CH$_2$N—), 3.28 (s, 3H, —NCH$_3$), 4.21 (s, 6H, —OCH$_3$), 4.27-4.29 (d, J=8.0 Hz, 1H, Ar—CH—), 7.23-7.25 (d, J=8.4 Hz, 1H, Ar—H), 7.55-7.58 (d, J=8.8 Hz, 1H, Ar—H), 7.69 (s, 1H, Ar—H).

Example 61

Preparation of the hydrochloride of N,N-dimethyl-3-(thien-2-yl)-3-morpholinyl-propylamine (VI61)

2-acetylthiophene (0.05 mol), dimethylamine hydrochloride (0.055 mol) and polyformaldehyde (0.065 mol) are dissolved in 95% ethanol (20 mL) and added with concentrated HCl (0.2 mL). Following procedures described in General Method Two-Method C, a white solid is obtained (7.66 g). The yield is 70.0%. MS(m/z):184.1 [M+1]$^+$.

The intermediate obtained above (10 mmol) and NaBH$_4$ (10 mmol) are dissolved in methanol (50 mL). Following procedures described in General Method Three, a white solid is obtained (1.99 g). The yield is 90.2%. MS(m/z): 186.0 [M+1]$^+$.

The product from the previous step (8 mmol), triethylamine (9.6 mmol) and p-methyl benzenesulfonyl chloride (8.8 mmol) are dissolved in acetonitrile (30 mL). Following procedures described in General Method Four, morpholine (24 mmol) and $K_2CO_3$ (8 mmol) are added. The hydrochloride of N,N-dimethyl-3-(thien-2-yl)-3-morpholinyl-propylamine (VI-61) is obtained according to General Method Four as a white solid (1.20 g). The yield is 46.2%. Mp=195.0-197.3° C., MS(m/z): 255.1 [M+1]$^+$.

$^1$H NMR (DMSO-d$_6$) +D$_2$O: δ: 2.05-2.09 (m, 1H, —CH$_2$CH$_2$N—), 2.23-2.29 (m, 4H, —NCH$_2$CH$_2$O), 2.32-2.36 (m, 1H, —CH$_2$CH$_2$N—), 2.69 (s, 6H, N(CH$_3$)$_2$), 2.78-2.81 (m, 2H, —CH$_2$CH$_2$N—), 3.48-3.52 (m, 4H, —NCH$_2$CH$_2$O), 3.59-3.61 (t, J=7.2 Hz, 1H, Ar—CH—), 7.02-7.05 (d, J=8.8 Hz, 1H, Ar—H), 7.15-7.18 (m, 1H, Ar—H), 7.29-7.32 (d, J=8.0 Hz, 1H, Ar—H).

Example 62

Preparation of the hydrochloride of N-methyl-N-benzyl-3-(thien-2-yl)-3-morpholinyl-propylamine (VI-62)

2-acetylthiophene (20 mmol), N-methylaniline hydrochloride (22 mmol) and polyformaldehyde (26 mmol) are dissolved in 95% ethanol (10 mL) and added with concentrated HCl (0.05 mL). Following procedures described in General Method Two-Method C, a white solid is obtained (4.48 g). The yield is 76.0%. MS(m/z): 260.1 [M+1]$^+$.

The intermediate obtained above (10 mmol) and NaBH$_4$ (10 mmol) are dissolved in methanol (50 mL). Following procedures described in General Method Three, a white solid is obtained (2.67 g). The yield is 90.0%. MS(m/z): 262.0 [M+1]$^+$.

The product from the previous step (8 mmol), triethylamine (9.6 mmol) and p-methyl benzenesulfonyl chloride (8.8 mmol) are dissolved in acetonitrile (30 mL). Following procedures described in General Method Four, morpholine (24 mmol) and $K_2CO_3$ (8 mmol) are added. The hydrochloride of N-methyl-N-benzyl-3-(thien-2-yl)-3-morpholinyl-propylamine (VI-62) is obtained according to General Method Four as a white solid (1.54 g). The yield is 48.0%. Mp=220.8-224.0° C., MS(m/z): 331.2 [M+1]$^+$.

$^1$H NMR (DMSO-d$_6$) +D$_2$O: δ: 2.11-2.16 (m, 2H, —CH$_2$CH$_2$N—), 2.22-2.30 (m, 4H, —NCH$_2$CH$_2$O), 2.69 (s, 3H, —NCH$_3$), 2.78-2.82 (m, 2H, —CH$_2$CH$_2$N—), 3.59-3.62 (m, 4H, —NCH$_2$CH$_2$O), 4.23 (s, 2H, Ar—CH$_2$—), 4.30-4.32 (t, J=7.2 Hz, 1H, Ar—CH—), 7.00-7.03 (d, J=8.8 Hz, 1H, Ar—H), 7.14-7.17 (m, 1H, Ar—H), 7.25-7.30 (m, 5H, Ar—H), 7.33-7.35 (d, J=8.0 Hz, 1H, Ar—H).

Example 63

Preparation of the hydrochloride of N-methyl-3-(thien-2-yl)-3-morpholinyl-propylamine (VI-63)

A hydrogenation reaction at normal temperature and pressure is performed in the solution of N-methyl-N-benzyl-3-(thien-2-yl)-3-morpholinyl-propylamine hydrochloride (5 mmol) in methanol (30 mL) with 5% Pd/C (0.2 g) for 2 h. After the reaction, the Pd/C is removed through filtration and the filtrate is concentrated to give a white solid. Recrystalization of the white solid with anhydrous ethanol (10 mL) yields the hydrochloride of N-methyl-3-(thien-2-yl)-3-morpholinyl-propylamine (VI-63) (1.10 g). The yield is 70.2%. Mp=151.2-154.3° C., MS(m/z): 241.0 [M+1]$^+$.

$^1$H NMR (DMSO-d$_6$) +D$_2$O: δ: 2.12-2.25 (m, 2H, —CH$_2$CH$_2$N—), 2.35-2.40 (m, 4H, —NCH$_2$CH$_2$O), 2.80-2.88 (m, 2H, —CH$_2$CH2N—), 3.45 (s, 3H, N—CH$_3$), 3.58-3.66 (m, 4H, —NCH$_2$CH$_2$O), 3.77-3.79 (t, J=7.2 Hz, 1H, Ar—CH—), 7.05-7.07 (d, J=8.8 Hz, 1H, Ar—H), 7.12-7.15 (m, 1H, Ar—H), 7.28-7.31 (d, J=8.0 Hz, 1H, Ar—H).

Example 64

Tablets

| Compounds of Examples 1-63 | 10 mg |
|---|---|
| Sucrose | 150 mg |
| Corn starch | 38 mg |
| Calcium stearate | 2 mg |

Preparation Method: The active ingredient is blended with sucrose and corn starch, and wetted by adding water thereto. After thoroughly stirring, the uniformly blended mixture is dried, ground and sieved. Calcium stearate is added and well mixed. The resulted mixture is compressed into a tablet, which has a weight of 200 mg and a content of the active ingredient of 10 mg.

Example 65

Injections

| Compounds of Examples 1-63 | 20 mg |
|---|---|
| Water for injection | 80 mg |

Preparation Method: The active ingredient is dissolved in water for injection to form a homogeneous solution. The solution is filtered and dispensed into ampoules under aseptic conditions. Each ampoule contains 10 mg of the solution and has a content of the active ingredient of 2 mg.

Example 66

Antidepressant Activity of the Compound

1. The Inhibition by the Compound Towards the Reuptake of 5-hydroxy tryptamine (5-HT), Noradrenaline (NA) and Dopamine (DA):

An in vitro screening assay is performed using monoclonal technology and radioactive ligand binding assay for novel compounds with specific target. This is a handy method which can evaluate the corresponding biological activity of the compound with objectivity and accuracy. The method used is reported (*Biochem Phearmacol* 2008, 75(9): 1835-184 and *Eur J Pharmacol,* 2007, 576(1-3): 43-54). An effective dual reuptake inhibitor for 5-HT and NA, Venlafaxine, and a triple reuptake inhibitor for 5-HT, NA and DA, DOV-21947, are used as positive controls for the study of the inhibition by the compounds of the present invention towards the reuptake of 5-HT, NA and DA. The method is as follows:

(1). Establishment of Stable Cell Lines Expressing 5-HT Transporter (hSERT), NA Transporter (hNAT) or DA Transporter (hDAT)

HEK 293 cells are separately transfected with pcDNA3.0-hSERT, hNAT and hDAT vector plasmid. The transfected cells were grown in G418 selective DMEM medium at 48 h after the transfection. Stable transfected monoclonal cells obtained by serially diluting G418-resistant cells 3 weeks later are isolated and grown in medium containing G418 to proliferate. The expression of the 5-HT, NA, or DA transporter on the monoclonal cells is confirmed with the 5-HT/NA/DA reuptake experiment. Eventually, cell lines that stably express 5-HT, NA, or DA transporter are obtained.

(2). Reuptake of 5-HT/NA/DA

The test compound of the present invention, and the positive controls Venlafaxine and DOV-21947 are dissolved in DMSO separately to a concentration of 0.01 mol/L and diluted further with deionized water to a final concentration of 100 μmol/L. 50 μL of the compound to be tested (or the positive controls) and 430 μL of the cell are added to the reaction tube. The mixture is incubated in a water bath at 30° C. for 10 min. Then, the radioactive ligand, [$^3$H]-5-HT, [$^3$H]-NA or [$^3$H]-DA are added individually with a volume of 20 μL leading to a final concentration of 10 μmol/L for the compound to be tested or the positive controls. The reaction is stopped by putting the reaction tube into an ice bath right after 10 min incubation in a water bath at 30° C. Bound radioligand is separated from the free by rapid filtration through Brandel 24-well harvester using GF/B glass fiber filter paper and washed with an ice-colded washing buffer (50 mM Tris, 5 mM EDTA, pH 7.4) for 3 times. The filter paper is then dried and put into a 0.5 mL centrifuge tube, to which 500 μL lipid-soluble scintillation liquid is added. The radioactivity is measured with a MicroBeta liquid scintillation counter. This experiment includes the test for: total reuptake (blank control), non-specific reuptake (10 μmol/L, positive control) and sample reuptake (10 μmol/L, compound of the present invention). Each concentration is tested in two parallel test tubes at the same time, and three dependent tests are performed.

The percentage of reuptake inhibition by each compound is calculated according to the equation:

Reuptake Inhibition (I%)=(Total Reuptake cpm−Sample Reuptake cpm)/(Total Reuptake cpm−Non-specific Reuptake cpm)×100%

(3). Results

The test results for the reuptake inhibition towards 5-HT, NA and DA by samples under the same concentration (0.1 mmol/L) are shown in Table 2, wherein the positive control Venlafaxine is a commercially available antidepressant and another positive control DOV-21947 is an antidepressant in its phase II clinical trial.

TABLE 2 the reuptake inhibition towards 5-HT, NA and DA by the compound

| Compound | 5-HT Reuptake Inhibition | NA Reuptake Inhibition | DA Reuptake Inhibition |
| --- | --- | --- | --- |
| VI-1 | 98.2 | 101.2 | 100.9 |
| VI-2 | 94.8 | 100.3 | 103.4 |
| VI-4 | 101.9 | 93.6 | 89.9 |
| VI-6 | 106.3 | 101.4 | 106.4 |
| VI-13 | 96.6 | 98.8 | 96.9 |
| VI-16 | 90.5 | 92.1 | 80.2 |
| VI-19 | 95.3 | 91.2 | 75.6 |
| VI-22 | 96.3 | 99.8 | 96.5 |
| VI-24 | 65.3 | 76.2 | 58.9 |
| VI-25 | 91.5 | 96.8 | 39.2 |
| VI-31 | 87.9 | 88.1 | 75.6 |
| VI-34 | 47.3 | 49.5 | 2.48 |
| VI-36 | 98.3 | 97.8 | 87.2 |
| VI-38 | 25.9 | 29.3 | 23.0 |
| VI-44 | 45.8 | 54.6 | 67.0 |
| VI-46 | 92.3 | 89.5 | 78.0 |
| VI-48 | 65.0 | 58.0 | 45.6 |
| VI-56 | 78.0 | 68.7 | 59.2 |
| VI-61 | 78.9 | 75.0 | 65.6 |
| Venlafaxine | 100.4 | 96.4 | 52.4 |
| DOV-21947 | 100.0 | 100.0 | 100.0 |

As can be seen from the results, at the concentration of 10 μmol/L, compounds of the present invention, namely compound VI-1, VI-2, VI-4, VI-6, VI-13, VI-16, VI-19, VI-22, VI-31, VI-36 and VI-46 have a relatively strong inhibition effect towards the reuptake of 5-HT, NA and DA, a effect that is comparable with that of Venlafaxine and DOV-21947.

2. In Vivo Antidepressant Activity of the Compound

The eleven compounds mentioned above having triple inhibition effect on 5-HT, NA and DA reuptake and Venlafaxine as a positive control, are used to conduct preliminary studies on the in vivo antidepressant activity of the compounds, by performing the mice tail suspension test and the mice forced swimming test from the acquired helpless experiment.

(1). Mice Tail Suspension Test

Test Procedure:

According to their body weights, evenly and randomly divide 156 male ICR mice into 13 groups: Blank control group, Venlafaxine group (20.0 mg·kg$^{-1}$), and Compound treatment groups (20.0 mg·kg$^{-1}$). Through intragastric administration, 10 mL·kg$^{-1}$ of each sample (physiological saline for the blank control group) is administrated. After 1 h of the treatment, the mouse is held with a medical tape at a position around 2 cm from the tip of its tail and hung upside-down in the suspension cage with its head 5 cm away from the bottom of the cage. The observation starts right after the mouse is suspended for 2 min and continues for 4 min. The time during which the mouse is immobile (no struggling or only tiny movements of its body/limbs) in this 4 min is accumulated (IT, immobility time). The percentage of the improvement is calculated according to the equation:

Improvement %=[IT (blank control group)−IT (compound treatment group)]/IT (blank control group)×100%

The results are shown in Table 3.

TABLE 3

Effects on mice tail suspension test produced by a single oral administration of the compound

| Group | Number of mice | Dosage (mg/kg) | IT (sec) | Improvement (%) |
| --- | --- | --- | --- | --- |
| Blank control | 12 | 20.0 | 99.20 ± 31.54 | — |
| Venlafaxine | 12 | 20.0 | 36.97 ± 21.10** | 62.73 |
| VI-1 | 12 | 20.0 | 48.17 ± 38.29** | 51.44 |
| VI-2 | 12 | 20.0 | 36.19 ± 25.78** | 63.52 |
| VI-4 | 12 | 20.0 | 38.65 ± 16.32** | 61.04 |
| VI-6 | 12 | 20.0 | 25.68 ± 14.25** | 74.11 |
| VI-13 | 12 | 20.0 | 38.29 ± 23.76** | 61.40 |
| VI-16 | 12 | 20.0 | 45.21 ± 28.19** | 54.42 |
| VI-19 | 12 | 20.0 | 50.28 ± 21.30** | 49.31 |
| VI-22 | 12 | 20.0 | 65.25 ± 28.39** | 34.22 |
| VI-31 | 12 | 20.0 | 78.36 ± 23.00 | 20.84 |
| VI-36 | 12 | 20.0 | 39.91 ± 18.35** | 59.29 |
| VI-46 | 12 | 20.0 | 86.19 ± 35.87 | 13.01 |

**highly significant difference when compard to the blank control, P < 0.05

In the tail suspension test, compounds VI-1, VI-2, VI-4, VI-6, VI-13, VI-16, VI-19 and VI-36 produce significant reduction in the immobility time. At the dosage of 20 mg/kg, the foresaid 8 compounds have similar efficacy to that of the positive control Venlafaxine (36.97±21.10 s) at an equivalent dosage, but show highly significant difference from that of the blank control. This indicates that the said compounds have relatively strong in vivo antidepressant activity and their efficacy is similar to that of Venlafaxine.

(2). Mice Forced Swimming Test

Test procedure:

According to their body weights, evenly and randomly divide 156 male Kunming mice into 13 groups: Blank control group, Venlafaxine group (20.0 mg·kg$^{-1}$), and Compound treatment groups (20.0 mg·kg$^{-1}$). Through intragastric administration, 10 mL·kg$^{-1}$ of each sample (physiological saline for the blank control group) is administrated. The mice are pre-screened for swimming one day before the actual test. The mouse is placed into water (25° C., 10 cm deep) in a glass tank (height 20 cm, diameter 14 cm) and forced to swim for 6 min. Those who stop swimming at around 70-160 s are chosen for the actual test which starts 24 h later. After 1 h of the administration, the forced swimming test is performed by placing the animal into the above-mentioned environment to swim for 6 min. The accumulative immobility time for the last 4 min is recorded. Data is statistically analyzed with t-test. The results are shown in Table 4.

TABLE 4

Effects on mice forced swimming test produced by a single oral administration of the compound

| Group | Number of mice | Dosage (mg/kg) | IT (sec) |
| --- | --- | --- | --- |
| Blank control | 12 | 20.0 | 138 ± 30.1 |
| Venlafaxine | 12 | 20.0 | 77.4 ± 47.2** |
| VI-1 | 12 | 20.0 | 57.1 ± 37.8** |
| VI-2 | 12 | 20.0 | 74.9 ± 37.8** |
| VI-4 | 12 | 20.0 | 52.8 ± 32.0** |
| VI-6 | 12 | 20.0 | 79.3 ± 53.1* |
| VI-13 | 12 | 20.0 | 44.9 ± 53.7** |
| VI-16 | 12 | 20.0 | 62.1 ± 42.9** |
| VI-19 | 12 | 20.0 | 60.7 ± 26.7** |
| VI-22 | 12 | 20.0 | 75.4 ± 40.3** |
| VI-31 | 12 | 20.0 | 99.7 ± 43.7* |
| VI-36 | 12 | 20.0 | 90.6 ± 48.0* |
| VI-46 | 12 | 20.0 | 97 ± 48.5* |

*significant difference when compard to the blank control
**highly significant difference when compard to the blank control In the forced swimming test, all the test compounds show antidepressant activity, wherein compounds VI-1, VI-2, VI-4, VI-13, VI-16, VI-19 and VI-22 produce significant reduction in the immobility time. At the dosage of 20 mg/kg, the foresaid 7 compounds have similar efficacy to that of the positive control Venlafaxine at an equivalent dosage, but show highly significant difference from that of the blank control. Compounds VI-6, VI-31, VI-36 and VI-46 show significant difference from that of the blank control. This indicates that the said compounds have relatively strong in vivo antidepressant activity and their efficacy is similar to or stronger than that of Venlafaxine.

3. In Vivo tests of the Compounds for 5-Hydroxytryptophan Potentiation, Yohimbine Toxicity Enhancement and Oxidation Tremors Tests of the 5-hydroxytryptophan (DL-5-HTP) potentiation in mice, Yohimbine toxicity enhancement in mice and oxidation tremors can verify a compound's inhibition effect on 5-HT, NA and DA reuptake. Compound VI-2 is selected for the tests.

(1). Test of the Compound. VI-2 for 5-Hydroxytryptophan (DL-5-HTP) Potentiation in Mice a) Principles Taking DL-5-HTP as the precursor of 5-HT, the MAOs inhibitor Pargyline can inhibit the enzymatic degradation of MAO. While in mice, characteristic symptoms—head twitches can be observed.

b) Test Method

Three different dosages of VI-2 are used: 30, 15 and 7.5 mg/kg. The mouse is treated as follows: first, intraperitoneal injection of the compound, 0.2 mL/10 g; 30 min later, subcutaneous injection of Pargyline, 75 mg/kg; and 90 min later, intraveneous injection of DL-5-HTP. The induced head twitches of the mouse are observed 15 min later.

c) Results

From the obvious symptom of head-twitches in the mice, it is clear that VI-2 at 30, 15 and 7.5 mg/kg can significantly enhance the effect of 5-HTP. This enhancement presents a significant dose-effect relationship, indicating that VI-2 can indeed inhibit in vivo reuptake of 5-HT (consistent with in vitro results).

TABLE 5

5-hydroxytryptophan (DL-5-HTP) potentiation in mice by VI-2

| Group | Dosage | Frequency of head twitches | | | |
|---|---|---|---|---|---|
| | | 0 | I | II | III |
| Control | N.S | 9 | 1 | 0 | 0 |
| VI-2 | 30 mg/kg | 0 | 0 | 0 | 10 |
| VI-2 | 15 mg/kg | 0 | 0 | 4 | 6 |
| VI-2 | 7.5 mg/kg | 1 | 3 | 6 | 0 |

Control vs VI-2 30 mg/kg: $P < 0.01$
Control vs VI-2 15 mg/kg: $P < 0.01$
Control vs VI-2 7.5 mg/kg: $P < 0.05$ (2). Test of the Compound VI-2 for Yohimbine Toxicity Enhancement in mice a) Principles Yohimbine can prevent the binding of NA to the receptor by occupying $\alpha_2$ receptor. If an antidepressant which inhibits the deactivation of NA or inhibits NA reuptake is taken together with Yohimbine, an individual may be poisoned even to death due to the raised NA concentration.

b) Test Method

This test consists of 5 experimental groups: Yohimbine control group, VI-2-1 (30 mg/kg) group, VI-2-2 (18 mg/kg) group, VI2-3 (11 mg/kg) group and VI-2-4 (6.5 mg/kg) group. The highest dose used in the DL-5-HTP potentiation test in mice is designated as the reference for the highest dose group, down from which 4 dosage groups are set with a dose ratio of 0.6 across groups. For each VI-2 group, the compound at the corresponding dosage is administered orally, or as in the case of the Yohimbine control group, N.S is given to the animals. One hour after the treatment, Yohimbine at 25 mg/kg (life-threatening dose for the animal) is administered by subcutaneous injection to the mice in all groups. The mortality in each group is observed and recorded at 1, 2, 4, 5 and 24 h after the administration of Yohimbine. The $ED_{50}$ value is calculated accordingly.

c) Results

The higher mortality rate in VI-2-1 (30 mg/kg) group, VI-2-2 (18 mg/kg) group and VI-2-3 (11 mg/kg) group indicates that the compound VI-2 enhances the toxicity of Yohimbine at those doses. The enhancement in toxicity presents a significant dose-effect relationship, indicating that VI-2 can indeed inhibit in vivo reuptake of NA (consistent with in vitro results). The $ED_{50}$ value calculated with DAS™ statistical software using Bliss method is 32.84 mg/kg.

TABLE 6

Yohimbine toxicity enhancement in mice by VI-2 (mortality, n = 10)

| Group | Dose | Mortality (%) | | | | |
|---|---|---|---|---|---|---|
| | | 1 h | 2 h | 4 h | 5 h | 24 h |
| Yohimbine | N.S | 0 | 0 | 0 | 0 | 0 |
| VI-2-1 | 30 mg/kg | 2 | 0 | 0 | 0 | 0 |
| VI-2-2 | 18 mg/kg | 1 | 2 | 0 | 0 | 0 |
| VI-2-3 | 11 mg/kg | 0 | 1 | 0 | 0 | 0 |
| VI-2-4 | 6.5 mg/kg | 0 | 0 | 0 | 0 | 0 |

(3). Oxidation Tremor Test a) Principles

The pathogenesis of paralysis agitans is primarily related to the imbalance between DA function and Ach function. Anything that causes the DA dysfunction or Ach hyperfunction can lead to tremors.

Oxotremorine is an M receptor agonist that can induce Parkinson's-syndrome-like signs such as tremors, ataxia, salivation, tearing and decreased body temperature.

The in vitro assay about DA reuptake inhibition shows that VI-2 can inhibit DA reuptake. If the same function can be exerted in vivo, VI-2 will be able to partially antagonize the symptoms induced by an M receptor agonist.

b) Test Method

This test consists of 6 experimental groups: Model control group, VI-2-1 (300 mg/kg) group, VI-2-2 (200 mg/kg) group, VI-2-3 (120 mg/kg) group, VI-2-4 (60 mg/kg) group and VI-2-5 (30 mg/kg) group. For each VI-2 group, the compound at the corresponding dosage is administered orally, or as in the case of the Model control group, N.S is given to the animals. One hour after the treatment, oxotremorine (0.5 mg/kg, 0.1 mL/10 g) is administered by intraperitoneal injection to the mice in all groups. Responses of the mice are observed.

c) Results

About 5 min after the oxotremorine administration, all of the 60 animals show signs of tremors, catalepsy, et al.

I. Tremors: Clear dose-effect relationship is observed. The intensity of tremors from high to low is: Model→30→60→120→200→300 mg/kg.

II. Activity: The best activity of the mice is observed in the 300 mg/kg group, followed by 200→120→60→30 mg/kg =Model.

III. Side overturn: Side overturn of different extent is observed in mice in VI-2-1 (300 mg/kg) group and VI-2-2 (200 mg/kg) group, but rarely observed in mice in groups with a dosage of 120 mg/kg or lower.

d) Analysis of the Results

I. The higher the VI-2 dose is, the less catalepsy, weaker tremor and better activity of the mice would be observed. No anti-tremor effect is observed at 30 mg/kg, nor is that obvious at 60 mg/kg. An improvement is only observed at doses up to 120 mg/kg and presents significant dose-effect relationship. It is indicated that VI-2 can partially antagonize the tremor symptom by enhancing the function of DA. However, there is no such enhancement at therapeutic doses (10-20 mg/kg). Nevertheless, the weak effect that VI-2 has against the DA reuptake may as well be helpful for antidepression.

II. The side overturn observed in VI-2-1 (300 mg/kg) group and VI-2-2 (200 mg/kg) group is a result from the activation of the central dopaminergic nerves due to the DA reuptake inhibition by high-dose VI-2 compound. This test further confirms the in vitro inhibition effect that VI-2 has against DA reuptake.

4. Learned Helplessness Experiment (1) Principles

This is an animal model of depression. In this experiment, an animal is placed under conditions with aversive stimulus which it can't escape. Eventually, the animal will stop trying to avoid the stimulus and exhibit a helpless behavior which would interfere with its future adaptive responses. This is a well recognized depression state, in which the level of catecholamine in the animal's brain is reduced. An antidepressant can act against this state. The learned helplessness model is sensitive to a variety of antidepressants used in a sub-long period (3-7 d), including tricyclic antidepressants, monoamine oxidase inhibitors, monoamine reuptake inhibitors and atypical antidepressants.

(2) Test Method

The animals are grouped. The pre-shock animals are generated the first day by performing inescapable electric shock. The pre-shock animals are given foot electric shock (0.8 mA, 15 s) for 60 times (1 min interval). Rats in the control group are only put into the cage for a same period of time but without any electric shock.

The administration of drugs starts the next day and lasts for one week. The treatment groups consist of positive control group (Venlafaxine, 30 mg/kg), VI-2-1 (20 mg/kg) group, VI-2-2 (10 mg/kg) group and VI-2-3 (5 mg/kg) group. The conditioned avoidance test is conducted 24 h after the last administration to determine the number of times of successful avoidance and the incubation period of escape.

(3) Results

In the conditioned avoidance test a week later, animals in the control group exhibit significantly shortened incubation period of escape and much more times of successful avoidance. Animals in the model group show obvious helpless behavior after the inescapable electric shock and exhibit significantly extended incubation period of escape and a huge reduction in the number of times of successful avoidance. Animals in the treatment groups with Venlafaxine or VI-2 at 3 doses exhibit significantly shortened incubation period of escape and relatively more times of successful avoidance. Therefore, VI-2 is capable of acting against this kind of depression state.

TABLE 7

Effects of VI-2 in the learned helplessness experiment (n = 10)

| Group | Dose | Incubation period of escape (s) | Number of times of successful avoidance |
|---|---|---|---|
| Control | N.S | 42.2 ± 46.88 | 23.5 ± 2.88 |
| Model | N.S | 525.4 ± 300.48 | 8.2 ± 6.94 |
| Venlafaxine | 30 mg/kg | 72.8 ± 77.26** | 19.4 ± 6.88** |
| VI-2-1 | 20 mg/kg | 171.1 ± 159.69* | 18.9 ± 9.35* |
| VI-2-2 | 10 mg/kg | 188.3 ± 178.38* | 19.5 ± 8.83* |
| VI-2-3 | 5 mg/kg | 140.3 ± 195.44* | 21.2 ± 6.73** |

*$P < 0.05$,
**$P < 0.01$ treatment vs model

5. Acute Toxicity Experiment

Calculated by using the method reported in Modern Pharmacological Experiments edited by Juntian Zhang for preliminary screening and the Bliss method for statistical analysis, the $LD_{50}$ values for VI-1, VI-2 and VI-16 administrated to the mice by single oral gavage are 1050 mg/kg, 950 mg/kg, and 870 mg/kg, respectively.

6. Bacterial Reverse Mutation Test of Compounds VI-1 VI-2 and VI16

Strains: Histidine auxotroph mutant of mouse salmonella $TA_{97}$, $TA_{98}$, $TA_{100}$ and $TA_{102}$.

Test method: The one reported in Maron DM et al: (1983) Mutay Res. 113, 173-216 is used.

Results: The test consists of two parts, i.e., $-S_9$ and $+S_9$. A bacteriostatic action is showed at a dosage of 5000 µg per dish for $TA_{98}$ in the test system without $S_9$ and $TA_{97}$ in the test system containing $S_9$. No bacteriostatic actions to all the strains are observed at all the other dosages, and the growth background is good. In the test system with or without $S_9$, VI-1, VI-2 and VI-16 at all test dosages do not cause any significant increase in the number of revertant colonies and the Ames test is negative.

The invention claimed is:

1. A compound represented by the following formula, or a pharmaceutically acceptable salt or hydrate thereof:

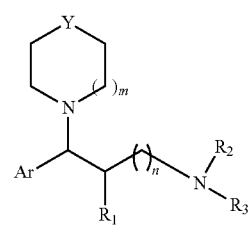

wherein
Ar represents

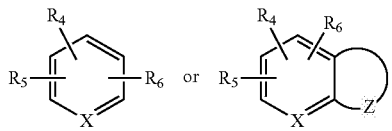

or an optionally substituted heteroaryl radical selected from the group consisting of thienyl, furyl, pyrimidinyl, pyridazinyl, pyrazinyl, oxazolyl, isoxazolyl, thiazolyl, isothiazolyl, imidazolyl and pyrazolyl,
and Ar is not an un-substituted phenyl;

$R_1$ represents H or $C_1$-$C_5$ alkyl;

$R_2$ and $R_3$ are each independently one of H, $C_1$-$C_5$ alkyl; $C_1$-$C_5$ haloalkyl, $C_1$-$C_5$ hydroxyalkyl, $C_1$-$C_5$ alkoxy, $C_5$ or $C_6$ alphatic ring, phenyl, substituted phenyl, benzyl or substituted benzyl, with the proviso that $R_2$ and $R_3$ are not H at the same time;

or $R_2$, $R_3$ and N form together a 5- to 7-membered alphatic ring which may contain one of N or O or S, and N may be substituted with $R_7$;

$R_4$, $R_5$ and $R_6$ are each independently one of H, $C_1$-$C_3$ alkyl or alkoxy, $C_1$-$C_3$ haloalkyl, $C_1$-$C_3$ haloalkoxy, benzyloxy, $C_5$ or $C_6$ alphatic ring, phenyl, substituted phenyl, hydroxyl, amino, substituted amino, halogen, carboxyl, carboxylic acid ester, nitro or cyano;

$R_7$ represents one of $C_1$-$C_5$ alkyl, $C_1$-$C_5$ haloalkyl, $C_1$-$C_5$ hydroxyalkyl, $C_1$-$C_5$ alkoxy, $C_5$ or $C_6$ alphatic ring, phenyl, substituted phenyl, benzyl or substituted benzyl;

Y represents C, N or O; wherein N may be substituted with $C_1$-$C_3$ alkyl, $C_1$-$C_3$ haloalkyl, $C_1$-$C_3$ hydroxyalkyl, phenyl, substituted phenyl, benzyl, substituted benzyl, aromatic heterocyclic or substituted aromatic heterocyclic;

X represents C or N;

Z represents a 5- or 6-membered saturated or unsaturated ring containing C, S, N or O;

m=0; n=1, or 2.

2. The compound according to claim 1, wherein the substituted amino group is an amino group substituted with $C_1$-$C_3$ alkyl or $C_1$-$C_3$ haloalkyl.

3. The compound according to claim 1, wherein the substituted phenyl or the substituted benzyl has 1-4 substituents on the benzene ring, with $R_4$, $R_5$ and $R_6$ representing the substituents.

4. The compound according to claim 1, wherein the salt is a pharmaceutically acceptable inorganic or organic salt.

5. The compound according to claim 4, wherein the hydrate contains 0.5-3 molecules of crystal water.

6. A compound selected from the group consisting of:
VI-1 N,N-diethyl-3-(3,4-dichlorophenyl)-3-(pyrrolidin-1-yl)-propylamine,
VI-2 N,N-dimethyl-3-(3,4-dichlorophenyl)-3-(pyrrolidin-1-yl)-propylamine,
VI-3 N,N-dimethyl-3-(3,4-dichlorophenyl)-3-(piperazin-1-yl)-propylamine,
VI-4 N,N-dimethyl-3-(3,4-dichlorophenyl)-3-morpholinyl-propylamine,
VI-5 N-methyl-N-benzyl-3-(3,4-dichlorophenyl)-3-morpholinyl-propylamine,
VI-6 4-(3-(3,4-dichlorophenyl)-3-(pyrrolidin-1-yl)propylmorpholine,
VI-7 N,N-dimethyl-3-(3,4-dichlorophenyl)-3-piperidyl-propylamine,
VI-8 N,N-dimethyl-3-(4-chlorophenyl)-3-morpholinyl-propylamine,
VI-9 4-(3-(4-chlorophenyl)-3-(pyrrolidin-1-yl)propylmorpholine,
VI-10 N,N-dimethyl-3-(4-methylphenyl)-3-morpholinyl-propylamine,
VI-11 4-(3-(4-methylpiperazin-1-yl)-1-(4-methylphenyl)propylmorpholine,
VI-12 4-(3-(4-methylphenyl)-3-(morpholinyl)propylpyrrole,
VI-13 N,N-dimethyl-3-(benzothiophen-3-yl)-3-(pyrrolidin-1-yl)-propylamine,
VI-14 N-methyl-N-benzyl-3-(benzothiophen-3-yl)-3-(pyrrolidin-1-yl)-propylamine,
VI-15 N-methyl-3-(benzothiophen-3-yl)-3-(pyrrolidin-1-yl)-propylamine,
VI-16 N,N-dimethyl-3-(benzothiophen-3-yl)-3-piperidyl-propylamine,
VI-17 N-methyl-N-benzyl-3-(benzothiophen-3-yl)-3-piperidyl-propylamine,
VI-18 N-methyl-3-(benzothiophen-3-yl)-3-piperidyl-propylamine,
VI-19 N,N-dimethyl-3-(benzothiophen-2-yl)-3-(pyrrolidin-1-yl)-propylamine,
VI-20 N-methyl-N-benzyl-3-(benzothiophen-2-yl)-3-(pyrrolidin-1-yl)-propylamine,
VI-21 N-methyl-3-(benzothiophen-2-yl)-3-(pyrrolidin-1-yl)-propylamine,
VI-22 N,N-dimethyl-3-(benzothiophen-2-yl)-3-piperidinyl-propylamine,
VI-23 N-methyl-N-benzyl-3-(benzothiophen-2-yl)-3-piperidyl-propylamine,
VI-24 N-methyl-3-(benzothiophen-2-yl)-3-piperidyl-propylamine,
VI-25 N,N-dimethyl-3-(benzothiophen-2-yl)-3-morpholinyl-propylamine,
VI-26 N-methyl-N-benzyl-3-(benzothiophen-2-yl)-3-morpholinyl-propylamine,
VI-27 N-methyl-3-(benzothiophen-2-yl)-3-morpholinyl-propylamine,
VI-28 N,N-dimethyl-3-(benzothiophen-3-yl)-3-morpholinyl-propylamine,
VI-29 N-methyl-N-benzyl-3-(benzothiophen-3 -yl)-3-morpholinyl-propylamine,
VI-30 N-methyl-3-(benzothiophen-3-yl)-3-morpholinyl-propylamine,
VI-31 N,N-dimethyl-3-(indol-3-yl)-3-morpholinyl -propylamine,
VI-32 N-methyl-N-benzyl-3-(indol-3-yl)-3-morpholinyl-propylamine,
VI-33 N-methyl-3-(indol-3-yl)-3-morpholinyl-propylamine,
VI-34 N,N- dimethyl-3-(5-chloro -6-methoxynaphthalen-2-yl)-3-morpholinyl-propylamine,
VI-35 N-methyl-N-benzyl-3-(5-chloro-6-methoxynaphthalen-2-yl)-3-morpholinyl-propylamine,
VI-36 N,N-dimethyl-3-(5-chloro-6-methoxynaphthalen-2-yl)-3-(pyrrolidin-1-yl)-propylamine,
VI-37 N,N-dimethyl-3-(4-methoxyphenyl)-3-(pyrrolidin-1-yl)-propylamine,
VI-3 8 N,N-dimethyl-3-(4-methoxyphenyl)-3-morpholinyl-propylamine,
VI-39 N,N,2-trimethyl-3-(4-methoxyphenyl)-3-morpholinyl-propylamine,
VI-40 N,N-dimethyl-2((3,4-dichlorophenyl)(morpholine)methyl)-1-heptylamine, VI-41 N,N-dimethyl-3-(2,3-dihydrobenzofuran-5-yl)-3-morpholinyl-propylamine,
VI-42 N-methyl-N-benzyl-3-(2,3-dihydrobenzofuran-5-yl)-3-morpholinyl-propylamine,
VI-43 N-methyl-3-(2,3-dihydrobenzofuran-5-yl)-3-morpholinyl-propylamine,
VI-44 N,N-dimethyl-4-(3,4-diehlorophenyl)-4-morpholinyl-butylamine,
VI-45 N,N-dimethyl-4-(3,4-dichlorophenyl)-4-(piperazin-1-yl)-butylamine,
VI-46 N,N-dimethyl-4-(benzothiophen-3-yl)-4-morpholinyl-butylamine,
VI-47 N,N-dimethyl-4-(benzothiophen-3-yl)-4-(piperazin-1-yl)-butylamine,
VI-48 N,N-dimethyl-3-(2,4-difluorophenyl)-3-morpholinyl-propylamine,
VI-49 N-methyl-N-benzyl-3-(2,4-difluorophenyl)-3-morpholinyl-propylamine,
VI-50 N-methyl-3-(2,4-difluorophenyl)-3-morpholinyl-propylamine,
VI-51 N,N-dimethyl-3-(3,4-dichlorophenyl)-3-(4-benzylpiperazinyl)-propylamine,
VI-52 N,N-dimethyl-3-(3,4-diehlorophenyl)-3-(4-(3-(trifluoromethyl)phenyl)piperazinyl)-propylamine,
VI-53 N-methyl-N-benzyl-3-(1,2-methylenedioxybenzen-4-yl)-3-piperidyl-propylamine,
VI-54 N-methyl-3-(1,2-methylenedioxybenzen-4-yl)-3-piperidyl-propylamine,
VI-55 N,N-dimethyl-3-(3,4-dimethoxyphenyl)-3-morpholinyl-propylamine,
VI-56 N-methyl-N-benzyl-3-(3,4-dimethoxyphenyl)-3-morpholinyl-propylamine,
VI-57 N-methyl-3-(3,4-dimethoxyphenyl)-3-morpholinyl-propylamine,
VI-58 N,N-dimethyl-3-(3,4-dimethoxyphenyl)-3-piperidyl-propylamine,
VI-59 N-methyl-N-benzyl-3-(3,4-dimethoxyphenyl)-3-piperidyl-propylamine,
VI-60 N-methyl-3-(3,4-dimethoxyphenyl)-3-piperidyl-propylamine,
VI-61 N,N-dimethyl-3-(thien-2-yl)-3-morpholinyl-propylamine,
VI-62 N-methyl-N-benzyl-3-(thien-2-yl)-3-morpholinyl-propylamine, and
VI-63 N-methyl-3-(thien-2-yl)-3-morpholinyl-propylamine, or its pharmaceutically acceptable salt or hydrate thereof.

7. A composition used for depression treatment, comprising a therapeutically effective amount of the compound of claim 1, and a pharmaceutically acceptable carrier.

8. A method of treating depression in a subject, comprising administering to the subject the composition according to claim 7.

9. The compound according to claim 1, wherein $R_4$, $R_5$ and $R_6$ are each independently one of H, $C_1$-$C_3$ alkyl or alkoxy, $C_1$-$C_3$ haloalkyl, $C_1$-$C_3$ haloalkoxy, benzyloxy, $C_5$ or $C_6$ aliphatic ring, phenyl, substituted phenyl, amino, substituted amino, halogen, carboxyl, carboxylic acid ester, nitro or cyano.

10. A composition used for depression treatment, comprising a therapeutically effective amount of the compound of claim 6, and a pharmaceutically acceptable carrier.

11. A method of treating depression in a subject, comprising administering to the subject the composition according to claim 10.

* * * * *